US011944701B2

(12) United States Patent
Bikker et al.

(10) Patent No.: US 11,944,701 B2
(45) Date of Patent: *Apr. 2, 2024

(54) # PROTECTION OF MATERIALS BY SPHINGOSINE BASED COMPOUNDS

(71) Applicant: STICHTING VU, Amsterdam (NL)

(72) Inventors: Floris Jacob Bikker, Amsterdam (NL); Engelmundus Cornelis Ignatius Veerman, Amsterdam (NL); Marianne Valentijn-Benz, Amsterdam (NL); Willem Van 'T Hof, Amsterdam (NL)

(73) Assignee: STICHTING VU, Amsterdam (NL)

( * ) Notice: Subject to any disclaimer, the term of this patent is extended or adjusted under 35 U.S.C. 154(b) by 3 days.

This patent is subject to a terminal disclaimer.

(21) Appl. No.: 17/592,162

(22) Filed: Feb. 3, 2022

(65) Prior Publication Data

US 2022/0151900 A1 May 19, 2022

Related U.S. Application Data

(63) Continuation of application No. 14/397,016, filed as application No. PCT/NL2013/050314 on Apr. 26, 2013, now Pat. No. 11,273,113.

(30) Foreign Application Priority Data

Apr. 27, 2012 (EP) .................................... 12166050
Oct. 10, 2012 (EP) .................................... 12187985

(51) Int. Cl.

| | |
|---|---|
| ***A61K 8/55*** | (2006.01) |
| ***A23L 33/10*** | (2016.01) |
| ***A61C 13/08*** | (2006.01) |
| ***A61K 8/24*** | (2006.01) |
| ***A61K 8/41*** | (2006.01) |
| ***A61K 8/42*** | (2006.01) |
| ***A61K 8/68*** | (2006.01) |
| ***A61Q 11/00*** | (2006.01) |
| ***A61Q 11/02*** | (2006.01) |

(52) U.S. Cl.

CPC ................ *A61K 8/55* (2013.01); *A23L 33/10* (2016.08); *A61C 13/08* (2013.01); *A61K 8/24* (2013.01); *A61K 8/41* (2013.01); *A61K 8/42* (2013.01); *A61K 8/68* (2013.01); *A61Q 11/00* (2013.01); *A61Q 11/02* (2013.01); *A23V 2002/00* (2013.01)

(58) Field of Classification Search

CPC ... A61K 8/55; A61K 8/24; A61K 8/41; A61K 8/42; A61K 8/68; A23L 33/10; A61C 13/08; A61Q 11/00; A61Q 11/02; A23V 2002/00

See application file for complete search history.

(56) References Cited

U.S. PATENT DOCUMENTS

| | | | |
|---|---|---|---|
| 3,839,796 | A | 10/1974 | Hazar |
| 5,900,246 | A | 5/1999 | Lambert |
| 7,988,737 | B2 | 8/2011 | Hercouet et al. |
| 8,183,215 | B2 | 5/2012 | Kawakami et al. |
| 2003/0044449 | A1 | 3/2003 | Miyanishi et al. |
| 2004/0146466 | A1 | 7/2004 | Baig |
| 2010/0047374 | A1 | 2/2010 | Sakakibara et al. |
| 2010/0131062 | A1 | 5/2010 | Andersson et al. |

FOREIGN PATENT DOCUMENTS

| | | |
|---|---|---|
| EP | 2322161 | 5/2011 |
| JP | H03-210271 | 9/1991 |
| JP | H08-143422 | 6/1996 |
| JP | 2001-158735 | 6/2001 |
| JP | 2003-511110 | 3/2003 |
| JP | 2005-320275 | 11/2005 |
| JP | 2007-284609 | 11/2007 |
| JP | 2009-167135 | 7/2009 |
| JP | 2010-143912 | 7/2010 |
| JP | 2011-140527 | 7/2011 |
| JP | 2011-207825 | 10/2011 |
| KR | 2001004570 | 6/2001 |
| KR | 20010045670 | 6/2001 |
| WO | 98/49999 | 11/1998 |
| WO | 01/24866 | 4/2001 |
| WO | 2005/110343 | 11/2005 |
| WO | 2007/009477 | 1/2007 |
| WO | 2008/087705 | 7/2008 |

OTHER PUBLICATIONS

U.S. Notice of Allowance, U.S. Appl. No. 14/397,016, 7 pages, dated Nov. 8, 2021.
U.S. Advisory Action, U.S. Appl. No. 14/397,016, 3 pages, dated Jul. 28, 2021.
U.S. Final Office Action, U.S. Appl. No. 14/397,016, 22 pages, dated May 18, 2021.
U.S. Non-Final Office Action, U.S. Appl. No. 14/397,016, 19 pages, dated Nov. 2, 2020.
U.S. Final Office Action, U.S. Appl. No. 14/397,016, 29 pages, dated Apr. 6, 2020.
U.S. Non-Final Office Action, U.S. Appl. No. 14/397,016, 25 pages, dated Sep. 20, 2019.
U.S. Final Office Action, 29 pages, U.S. Appl. No. 14/397,016, dated Dec. 13, 2018.

(Continued)

*Primary Examiner* — Sarah Alawadi
*Assistant Examiner* — Thurman Wheeler
(74) *Attorney, Agent, or Firm* — Thompson Hine LLP

(57) ABSTRACT

The invention relates to the use of sphingosine-based compounds, in particular phytosphingosine compounds, in the protection of hydroxyapatite containing materials such as teeth and bone. Such compounds are especially useful in the treatment and prevention of dental caries, dental erosion, dentine hypersensitivity and tartar (dental calculus) formation. Methods and devices are also provided for preventing biofilm formation using sphingosine-based compounds. Compositions comprising sphingosine-based compounds are also provided.

4 Claims, 18 Drawing Sheets

(56) References Cited

OTHER PUBLICATIONS

U.S. Non-Final Office Action, U.S. Appl. No. 14/397,016, 18 pages, dated Apr. 5, 2018.
U.S. Non-Final Office Action, U.S. Appl. No. 14/397,016, 12 pages, dated Jun. 5, 2017.
U.S. Final Office Action, U.S. Appl. No. 14/397,016, 16 pages, dated Sep. 23, 2016.
U.S. Non-Final Office Action, U.S. Appl. No. 14/397,016, 9 pages, dated Feb. 17, 2016.
(PCT) International Search Report, International Application No. PCT/NL2013/050314, 3 pages, dated Aug. 26, 2013.
(PCT) Written Opinion, International Application No. PCT/NL2013/050314, 8 pages, dated Aug. 26, 2013.
(JP) Notice of Reasons for Rejection, Japanese Patent Application No. 2015-508890, 6 pages, dated Apr. 4, 2017.
(JP) English Translation of Office Action, Japanese Patent Application No. 2015-508890, dated Mar. 23, 2018.
(JP) English Translation of Office Action, Japanese Patent Application No. 2015-508890, dated Feb. 27, 2019.
Bibel et al., Can. J. Microbiology, p. 983, 1992.
Hirose et al., "Individual variations in salivary buffer capacity measured by Checkbuff(R) and relationship among salivary flow rate, pH, buffer capacity, phosphate ion, and protein concentrations in sliva," J. Dent. Hlth. 56, pp. 220-227, 2006.
Ilkka Havukkala, "Trends in Xuylitology," Trends in Glycoscience and Glycotechnology, vol. 3, No. 13, Sep. 1999.
Li et al., J. Mat. Chem., p. 4079, 2008.
Nguyen et al., "Small-Molecule Modulators of Listeria Monocytogenes Biofilm Development," Appl. Environ. Microbiol., 78 (5), pp. 1454-1465, Feb. 2012.
Oh et al., "Antibacterial Effect of Oral Rinses Containing Phytosphingosine," Key Engineering Materials, vols. 342-343, pp. 941-944, 2007.
Oh, Oral rinse containing phytosphingosine, Key Engineering Materials, p. 941, Jul. 2007.
Venegas et al., J. Dent. Res., p. 1124, 2006.

Phytosphingosine

Sphinganine

Phytosphingosine-phosphate

Sphingosine

N-acetyl-phytosphingosine

N-octanoyl-phytosphingosine

Stearoyl-phytosphingosine

D-erythro-sphingosine C15

Nonionic Detergents

| Detergent | Cat. no. | M.W. (anhydrous)[a] | CMC (mM)[b] | Aggregation no. | Average micellar weight | Size |
|---|---|---|---|---|---|---|
| APO-10 | 178375 | 218.3 | 4.6 | 131 | 28,000 | 1 g |
| APO-12 | 178377 | 246.4 | 0.568 | 2232 | 500,000 | 1 g |
| Big CHAP | 200965 | 878.1 | 3.4 | 10 | 8,800 | 1 g |
| Big CHAP, Deoxy | 256455 | 862.1 | 1.1–1.4 | 8–16 | 10,500 | 250 mg<br>1 g |
| BRIJ® 35, PROTEIN GRADE® Detergent, 30% Solution | 203724 | — | 0.09 | 40 | 48,000 | 100 ml<br>1 L |
| BRIJ® 35, PROTEIN GRADE® Detergent, 10% Solution, Sterile-Filtered | 203728 | — | 0.09 | 40 | 48,000 | 50 ml |
| $C_{12}E_5$ | 205524 | — | — | — | — | 1 g |
| $C_{12}E_6$ | 205527 | 450.7 | 0.087 | — | — | 1 g |
| $C_{12}E_8$ | 205528 | 538.8 | 0.11 | 123 | 66,000 | 1 g |
| $C_{12}E_9$ | 205529 | 582.8 | 0.08 | — | — | 1 g |
| Cyclohexyl-*n*-ethyl-β-D-maltoside, ULTROL® Grade | 239774 | 452.5 | 120 | — | — | 1 g |
| Cyclohexyl-*n*-hexyl-β-D-maltoside, ULTROL® Grade | 239775 | 508.6 | 0.56 | 63 | 32,000 | 500 mg<br>1 g |
| Cyclohexyl-*n*-methyl-β-D-maltoside, ULTROL® Grade | 239776 | 438.5 | 340 | — | — | 1 g |
| *n*-Decanoylsucrose | 252721 | 496.6 | 2.5 | — | — | 1 g<br>5 g |
| *n*-Decyl-β-D-maltopyranoside, ULTROL® Grade | 252718 | 482.6 | 1.6 | — | — | 1 g<br>5 g |
| *n*-Decyl-β-D-thiomaltoside, ULTROL® Grade | 252725 | 498.6 | 0.9 | — | — | 500 mg |
| Digitonin, High Purity | 300410 | 1229.3 | — | 5–6 | 7,000 | 250 mg<br>1 g<br>5 g |
| Digitonin, Alcohol-Soluble, High Purity | 300411 | 1229.3 | — | 5–6 | 7,000 | 250 mg<br>1 g |
| *n*-Dodecanoylsucrose | 324374 | 524.6 | 0.3 | — | — | 1 g<br>5 g |
| *n*-Dodecyl-β-D-glucopyranoside | 324351 | 348.5 | 0.13 | 200 | 70,000 | 1 g |
| *n*-Dodecyl-β-D-maltoside, ULTROL® Grade | 324355 | 510.6 | 0.1–0.6 | 98 | 50,000 | 500 mg<br>1 g<br>5 g<br>25 g |
| ELUGENT™ Detergent, 50% Solution | 324707 | — | — | — | — | 100 ml |
| GENAPOL® C-100, PROTEIN GRADE® Detergent, 10% Solution | 345794 | 627.0 | — | — | — | 50 ml |
| GENAPOL® X-80, PROTEIN GRADE® Detergent, 10% Solution | 345796 | 553.0 | 0.06–0.15 | — | — | 50 ml |
| GENAPOL® X-100, PROTEIN GRADE® Detergent, 10% Solution | 345798 | 641.0 | 0.15 | 88 | 56,000 | 50 ml |
| *n*-Heptyl-β-D-glucopyranoside | 375655 | 278.3 | 79 | — | — | 1 g |
| *n*-Heptyl-β-D-thioglucopyranoside, ULTROL® Grade, 10% Solution | 375659 | 294.4 | 30 | — | — | 10 ml<br>50 ml |
| *n*-Hexyl-β-D-glucopyranoside | 376965 | 264.3 | 250 | — | — | 1 g |

Figure 19 cont.

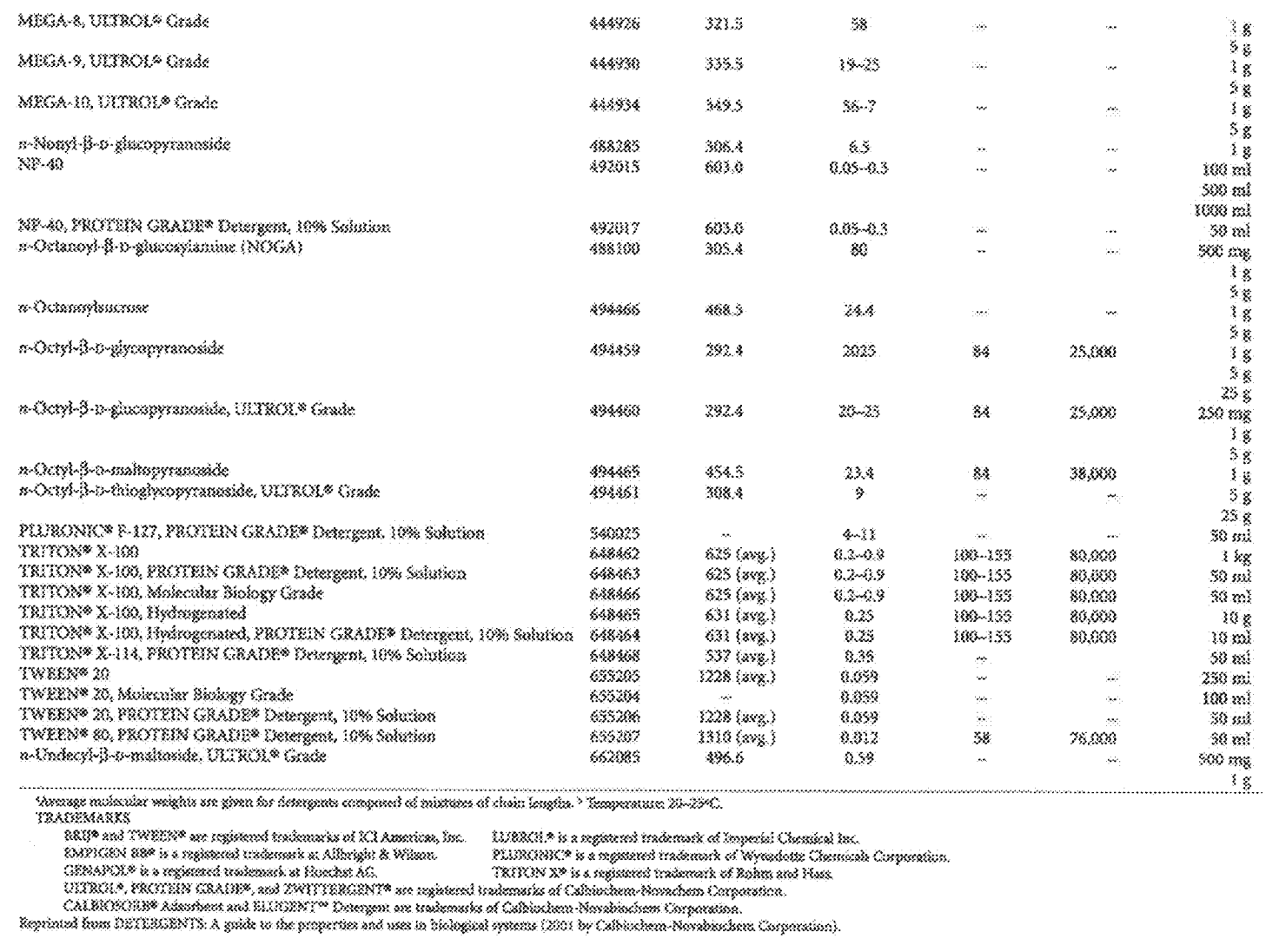

| | | | | | | |
|---|---|---|---|---|---|---|
| MEGA-8, ULTROL® Grade | 444926 | 321.5 | 58 | — | — | 1 g<br>5 g |
| MEGA-9, ULTROL® Grade | 444930 | 335.5 | 19–25 | — | — | 1 g<br>5 g |
| MEGA-10, ULTROL® Grade | 444934 | 349.5 | 56–7 | — | — | 1 g<br>5 g |
| n-Nonyl-β-D-glucopyranoside | 488285 | 306.4 | 6.5 | — | — | 1 g |
| NP-40 | 492015 | 603.0 | 0.05–0.3 | — | — | 100 ml<br>500 ml<br>1000 ml |
| NP-40, PROTEIN GRADE® Detergent, 10% Solution | 492017 | 603.0 | 0.05–0.3 | — | — | 50 ml |
| n-Octanoyl-β-D-glucosylamine (NOGA) | 488100 | 305.4 | 80 | — | — | 500 mg<br>1 g<br>5 g |
| n-Octanoylsucrose | 494466 | 468.5 | 24.4 | — | — | 1 g<br>5 g |
| n-Octyl-β-D-glycopyranoside | 494459 | 292.4 | 2025 | 84 | 25,000 | 1 g<br>5 g<br>25 g |
| n-Octyl-β-D-glucopyranoside, ULTROL® Grade | 494460 | 292.4 | 20–25 | 84 | 25,000 | 250 mg<br>1 g<br>5 g |
| n-Octyl-β-D-maltopyranoside | 494465 | 454.5 | 23.4 | 84 | 38,000 | 1 g |
| n-Octyl-β-D-thioglycopyranoside, ULTROL® Grade | 494461 | 308.4 | 9 | — | — | 5 g<br>25 g |
| PLURONIC® F-127, PROTEIN GRADE® Detergent, 10% Solution | 540025 | — | 4–11 | — | — | 50 ml |
| TRITON® X-100 | 648462 | 625 (avg.) | 0.2–0.9 | 100–155 | 80,000 | 1 kg |
| TRITON® X-100, PROTEIN GRADE® Detergent, 10% Solution | 648463 | 625 (avg.) | 0.2–0.9 | 100–155 | 80,000 | 50 ml |
| TRITON® X-100, Molecular Biology Grade | 648466 | 625 (avg.) | 0.2–0.9 | 100–155 | 80,000 | 50 ml |
| TRITON® X-100, Hydrogenated | 648465 | 631 (avg.) | 0.25 | 100–155 | 80,000 | 10 g |
| TRITON® X-100, Hydrogenated, PROTEIN GRADE® Detergent, 10% Solution | 648464 | 631 (avg.) | 0.25 | 100–155 | 80,000 | 10 ml |
| TRITON® X-114, PROTEIN GRADE® Detergent, 10% Solution | 648468 | 537 (avg.) | 0.35 | — | | 50 ml |
| TWEEN® 20 | 655205 | 1228 (avg.) | 0.059 | — | — | 250 ml |
| TWEEN® 20, Molecular Biology Grade | 655204 | — | 0.059 | — | — | 100 ml |
| TWEEN® 20, PROTEIN GRADE® Detergent, 10% Solution | 655206 | 1228 (avg.) | 0.059 | — | — | 50 ml |
| TWEEN® 80, PROTEIN GRADE® Detergent, 10% Solution | 655207 | 1310 (avg.) | 0.012 | 58 | 76,000 | 50 ml |
| n-Undecyl-β-D-maltoside, ULTROL® Grade | 662085 | 496.6 | 0.59 | — | — | 500 mg<br>1 g |

Average molecular weights are given for detergents composed of mixtures of chain lengths. [b] Temperature 20–25°C.

TRADEMARKS

BRIJ® and TWEEN® are registered trademarks of ICI Americas, Inc. LUBROL® is a registered trademark of Imperial Chemical Inc.

EMPIGEN BB® is a registered trademark of Albright & Wilson. PLURONIC® is a registered trademark of Wyandotte Chemicals Corporation.

GENAPOL® is a registered trademark of Hoechst AG. TRITON X® is a registered trademark of Rohm and Haas.

ULTROL®, PROTEIN GRADE®, and ZWITTERGENT® are registered trademarks of Calbiochem-Novabiochem Corporation.

CALBIOSORB® Adsorbent and ELUGENT™ Detergent are trademarks of Calbiochem-Novabiochem Corporation.

Reprinted from DETERGENTS: A guide to the properties and uses in biological systems (2001 by Calbiochem-Novabiochem Corporation).

PROTECTION OF MATERIALS BY SPHINGOSINE BASED COMPOUNDS

RELATED APPLICATIONS

This patent application is a continuation of U.S. patent application Ser. No. 14/397,016 filed on Oct. 24, 2014, which is the national stage application of International Application No. PCT/NL2013/050314 filed on Apr. 26, 2013, which claims priority to European Patent Application No. 12166050.0 filed on Apr. 27, 2012 and European Patent Application No. 12187985.2 filed on Oct. 10, 2012, each of which is incorporated herein by this reference in its entirety.

FIELD OF THE INVENTION

The invention relates to the use of sphingosine based compounds, in particular phytosphingosine compounds, in the protection of surfaces and materials such as hydroxyapatite containing materials such as teeth and bone. Such compounds and are especially useful as protective layer of surfaces as in the treatment and prevention of dental caries, dental erosion, dentine hypersensitivity, and tartar formation. Compositions comprising sphingosine based compounds are also provided. Methods and devices are also provided for preventing biofilm formation using sphingosine based compounds.

BACKGROUND OF THE INVENTION

The main constituent of dental enamel is the basic mineral calcium hydroxyapatite (HAP), $Ca_{10}(PO_4)_6(OH)_2$, which is inherently susceptible to the etching and dissolving action of acids. Examples of tooth decay that are caused by acids are dental caries and dental erosion. In dental caries, acidic end products of anaerobic bacterial metabolism in the dental plaque cause local dissolution of dental enamel, typically at sites which are difficultly accessible for dental hygiene. Dental erosion is the chemical dissolution of dental surfaces by acids from dietary or gastric origin, which, often in combination with mechanical wear (attrition and abrasion), can cause a widespread loss of superficial dental tissues. Under normal conditions saliva protects partially the enamel against the detrimental effects of acidic attacks by the neutralizing action of its buffer systems and by depositing a tooth pellicle, which is a lubricative film of salivary (glyco) proteins that covers the dental surfaces. Current consumption behavior has mounted up the acidic attacks to a level that surpasses the protective capacity of saliva. Worldwide this has led to a burgeoning incidence of dental erosion.

Dental enamel is also susceptible to tartar formation (dental calculus). Dental calculus refers to a build-up of hardened (mineralized) plaque on the teeth, formed by the presence of saliva, debris, and minerals. Dental calculus is a deposit of calcium phosphate salts on the surface of the teeth. It comprises a mixture of calcium phosphate minerals such as brushite, octacaclium phosphate, tricalciumphosphate and biological apatite.

Conventional oral care compositions, such as toothpastes and mouthwashes, are particularly suited for prevention of caries and tartar formation. However, no formulation has yet successfully added significant protection against dental erosion. Therefore, new formulations to protect dental surfaces are urgently needed.

SUMMARY OF THE INVENTION

In one aspect, the disclosure provides sphingosine compounds having formula I, for use as a coating on hydroxyapatite containing materials, such as bone or tooth, preferably for use as a tooth coating. Said compounds may be used to prepare medicaments for the coating of bone or tooth. Alternatively, said compounds may be used to prepare non-medicament formulations, such as oral care products and food products.

Preferably, the use of the compounds and the resulting coatings prevent or reduce tooth demineralization, a tooth demineralization disorder (preferably selected from dental erosion, dental caries, and dentine hypersensitivity), gum disease, and/or the formation of dental calculus. Preferably, said compounds are used to protect the tooth from the acid erosion associated with a tooth demineralization disorder. More preferably, the compounds are used to prevent or reduce tooth demineralization or a tooth demineralization disorder (preferably selected from dental erosion, dental caries, and dentine hypersensitivity).

In one aspect, the disclosure provides sphingosine compounds having formula I, for use as anti-tartar agents.

In one aspect, the disclosure provides sphingosine compounds having formula I, for use as anti-gingivitis agents.

In one aspect, the disclosure provides sphingosine compounds having formula I, for use as anti-periodontitis agents.

In one aspect, the disclosure provides sphingosine compounds having formula I, for use in treating or preventing xerostomia. Preferably, said compounds reduce or prevent a symptom of xerostomia.

In one aspect, the disclosure provides a method for coating a hydroxyapatite surface or a hydroxyapatite containing material comprising contacting said surface or said material with a sphingosine compound having formula I. Preferably, the hydroxyapatite surface or hydroxyapatite containing material is bone or tooth or an artificial or prosthetic bone or tooth. Preferably, the method reduces or prevents acid erosion of the hydroxyapatite or reduces or prevents the build-up of salt precipitates on the surface or material.

In one aspect, the disclosure provides cosmetic treatments for preventing the discoloration of a tooth comprising providing a sphingosine compound having formula I to said tooth.

In one aspect, the methods, uses, and treatments described herein further comprise the provision of hydroxyapatite nanoparticles.

In one aspect the disclosure provides compositions comprising a sphingosine compound having formula I. Preferably, the composition is an oral care composition, preferably selected from dentifrice (such as tooth powder and toothpaste), chewing gum, artificial saliva, and mouthwash. Preferably, the composition is a food composition, preferably selected from include dairy products, processed food products, oils, food and/or vitamin supplements, snack products, and beverage products. Preferably the compositions further comprise hydroxyapatite nanoparticles.

In one aspect, the disclosure provides a prosthetic bone or tooth coated with a sphingosine compound having formula I. Preferably the bone of tooth is also coated with hydroxyapatite nanoparticles.

In one aspect, the disclosure provides a method for preventing or reducing dental calculus formation, xerostomia, tooth demineralization or a tooth demineralization disorder, comprising administering to a subject in need thereof an effective amount of a sphingosine compound as disclosed herein. Preferably, said method reduces, prevents, or alleviates a symptom of xerostomia, dental erosion, dental caries, and/or dentine hypersensitivity and dental calculus.

In one aspect, the disclosure provides a method for reducing or preventing bacterial adhesion and/or biofilm formation on a surface, comprising coating at least part of said surface with a sphingosine compound having formula I. Preferably, the compound is selected from phytosphingosine (PHS), PHS phosphate, stearoyl PHS, sphinganine, and sphingosine. Preferably, the surfaces are hydroxyapatite containing materials. Preferably, the surfaces also include plastics and glass. More preferably the surfaces comprise hydroxyapatite, plastic, glass, silicone, fluorapatite, silicate, and surfaces containing titanium, carbonate- (such as calcium carbonate), phosphate- (such as calcium phosphate) and/or sulphate- (such as calcium sulphate) groups.

Preferably, the method is for phosphate- and/or sulphate containing surfaces and materials. Preferably, the surface is of a medical device. Preferably the surface is also coated with hydroxyapatite nanoparticles.

In one aspect, the disclosure provides a protective coating for phosphate- and/or sulphate containing surfaces and materials.

In one aspect, the disclosure provides a protective coating for surfaces and materials containing hydroxyapatite, plastic, glass, silicone, fluorapatite, silicate, and surfaces containing titanium, carbonate- (such as calcium carbonate), phosphate- (such as calcium phosphate) and/or sulphate- (such as calcium sulphate) groups. Preferably, said surface is from a medical device.

In one aspect, the disclosure provides an article which is at least partially coated with a sphingosine compound having formula I. Preferably, the compound is selected from PHS, PHS phosphate, stearoyl PHS, sphinganine, and sphingosine. Preferably, said article is a medical device. Preferably the surface is also coated with hydroxyapatite nanoparticles.

In one aspect, the disclosure provides a method for coating a surface or a material, in particular a medical device or surgical instrument, comprising contacting said surface or said material with a sphingosine compound having formula I. Preferably, the compound is selected from PHS, PHS phosphate, stearoyl PHS, sphinganine, and sphingosine. Preferably, the method reduces or prevents bacterial adhesion or reduces or prevents the build-up of biofilm on the surface or material. Preferably the surface is also coated with hydroxyapatite nanoparticles. Preferably said surface or material comprises hydroxyapatite, plastic, glass, silicone, fluorapatite, silicate, and surfaces containing titanium, carbonate- (such as calcium carbonate), phosphate- (such as calcium phosphate) and/or sulphate- (such as calcium sulphate) groups.

The sphingosine compound having formula I is:

Formula I

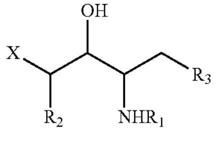

wherein X is a alkyl having 8-24 carbons, preferably 10 to 20 carbons, more preferably a linear alkyl;

$R_1$ is selected from H and $C(=O)C_{1-20}$, preferably $R_1$ is H;

$R_2$ is selected from H and OH, preferably $R_2$ is OH; and $R_3$ is selected from OH or F, preferably OH. Preferably, X is a linear alkyl having 10 to 20 carbons, $R_1$ is H, $R_2$ is OH, and R3 is OH. More preferably, the compound is phytosphingosine (PHS).

Preferably, formula I is

Formula I

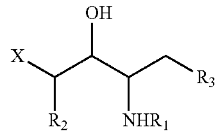

wherein X is an alkyl or alkenyl having 8-24 carbons, preferably 10 to 20 carbons, more preferably a linear alkyl;

$R_1$ is selected from H and $C(=O)C_{1-20}$, preferably $R_1$ is H;

$R_2$ is selected from H and OH, preferably $R_2$ is OH; and $R_3$ is selected from phosphate, OH or F, preferably OH.

Preferably, X is a linear alkyl having 10 to 20 carbons, $R_1$ is H, $R_2$ is OH, and $R_3$ is OH.

More preferably, X is an alkyl or alkenyl having 8-24 carbons, preferably 10 to 20 carbons, more preferably a linear alkyl;

$R_1$ is H;

$R_2$ is selected from H and OH, preferably $R_2$ is OH; and $R_3$ is selected from phosphate, OH or F, preferably OH.

Preferably, X is an alkyl or alkenyl having 8-24 carbons, preferably 10 to 20 carbons, $R_1$ is H;

$R_2$ is OH; and $R_3$ is selected from phosphate, OH or F, preferably OH.

Preferably, X is an alkyl or alkenyl having 8-24 carbons, preferably 10 to 20 carbons, $R_1$ is H;

$R_2$ is OH; and $R_3$ is selected from phosphate or OH.

Preferably, X is an alkyl or alkenyl having 8-24 carbons, preferably 10 to 20 carbons, $R_1$ is H;

$R_2$ is OH; and $R_3$ is OH.

Pre-weighed HAP discs were incubated with PHS at the indicated concentrations (0, 5, 50 and 500 μg/ml) in saliva buffer for 3 hr. Discs were subsequently exposed to 0.3 M citric acid for 30 minutes. After rinsing in demineralised water, discs were dried overnight and their weights determined.

Figure 3:
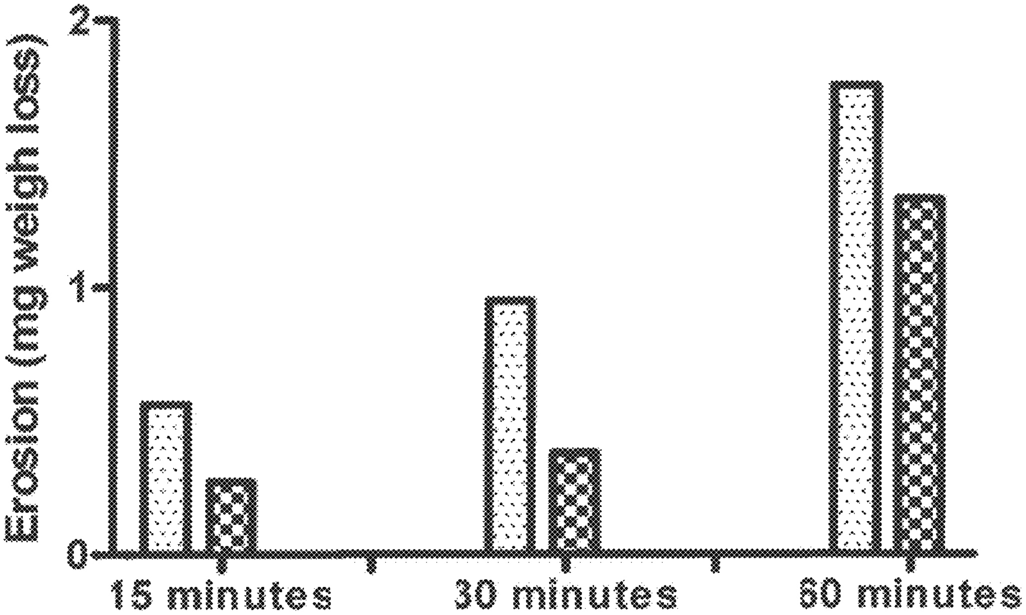

FIG. 3. Protection by PHS after exposure to citric acid for different periods. HAP discs (untreated and treated with 50 μg/ml PHS) were incubated with 0.1 M citric acid for the indicated times (15, 30 and 60 minutes, respectively). After rinsing with water, discs were dried and their weight determined. (White spotted bars represent the untreated disks, blocked bars represent the PHS treated disks.)

Figure 4:
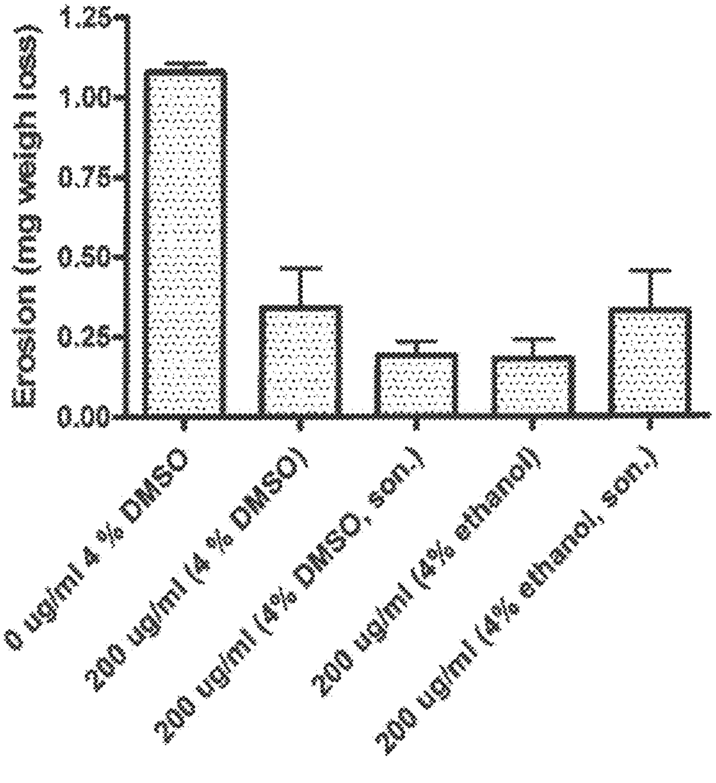

FIG. 4. Effect of stock solution preparation on anti-erosive activity of PHS. Stock PHS solutions (5 mg/ml)

were prepared in either DMSO or ethanol. These stock solutions were used for preparation of 200 μg/ml PHS solutions in saliva buffer, with or without sonication (son.) for 30 minutes. HAP discs were treated with the indicated solutions for 3 hours and then exposed to 0.1 M citric acid for 30 minutes. Discs were rinsed and dried and their weights determined.

Figure 5:
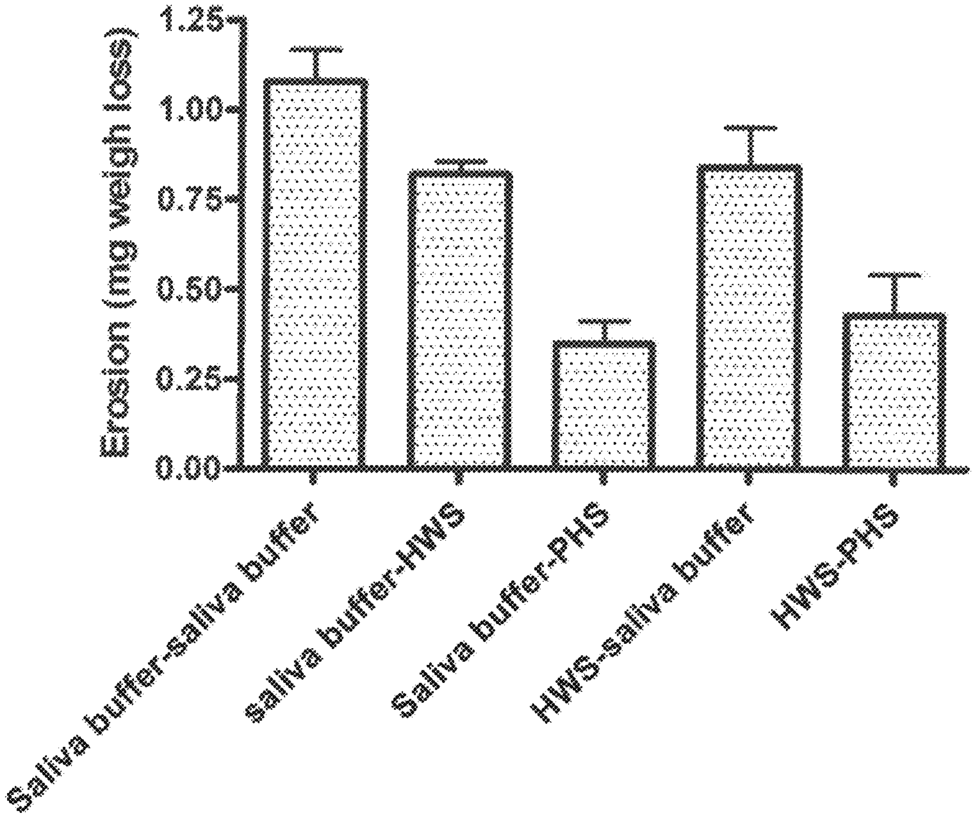

FIG. 5. Effect of the presence of a salivary pellicle on HAP on the protective effects of PHS. HAP disks were incubated with saliva (HWS) or saliva buffer (control) for 3 hrs. After rinsing disks were subsequently incubated for 3 hr with saliva buffer (saliva buffer-saliva buffer, HWS-saliva buffer), HWS (saliva buffer-HWS), or PHS (saliva buffer-PHS, HWS-PHS). Then disks were rinsed and exposed to 0.1 M citric acid (pH=3.0) for 30 minutes. Discs were rinsed with demineralised water and dried overnight and their weights determined.

Figure 6:
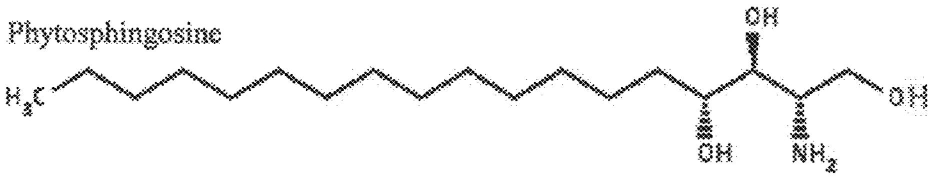
Figure 6:
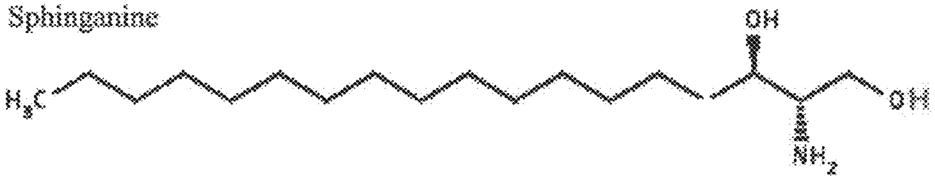
Figure 6:
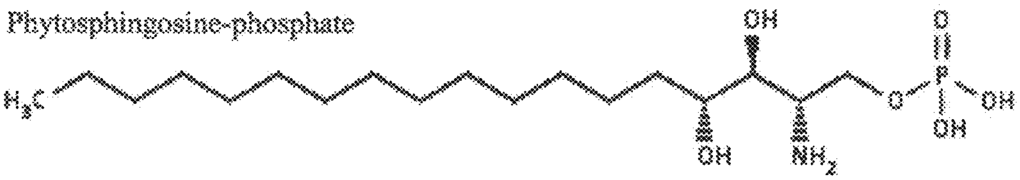
Figure 6:
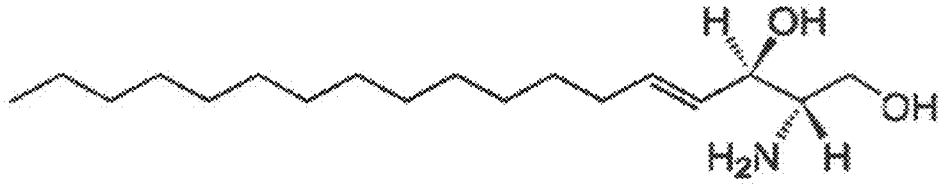
Figure 6:
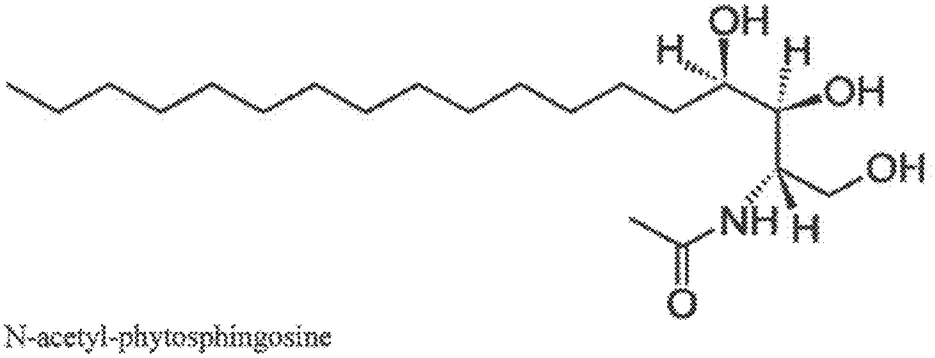
Figure 6:
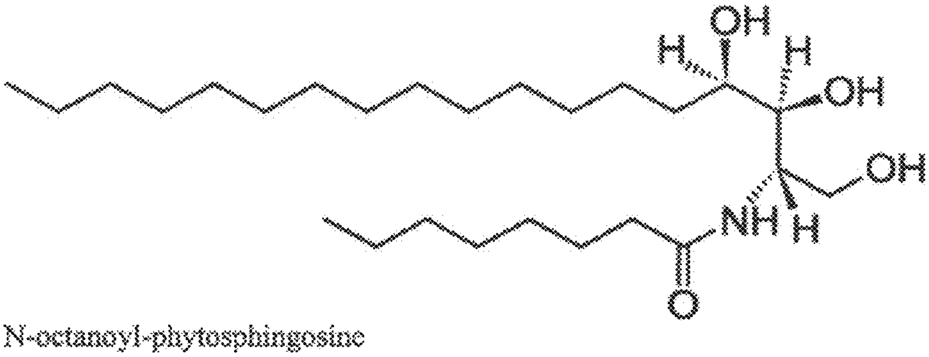
Figure 6:
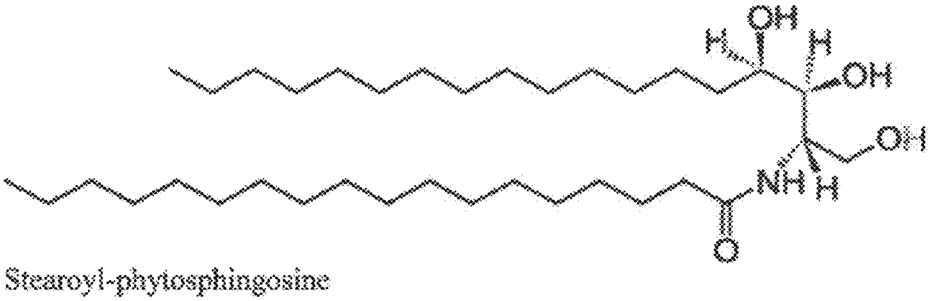
Figure 6:
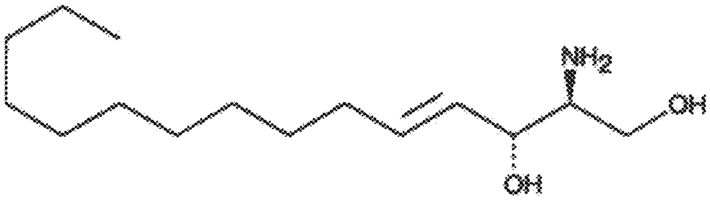

FIG. 6. Molecular structures of sphingosines used in the experiment of FIG. 7.

Figure 7:
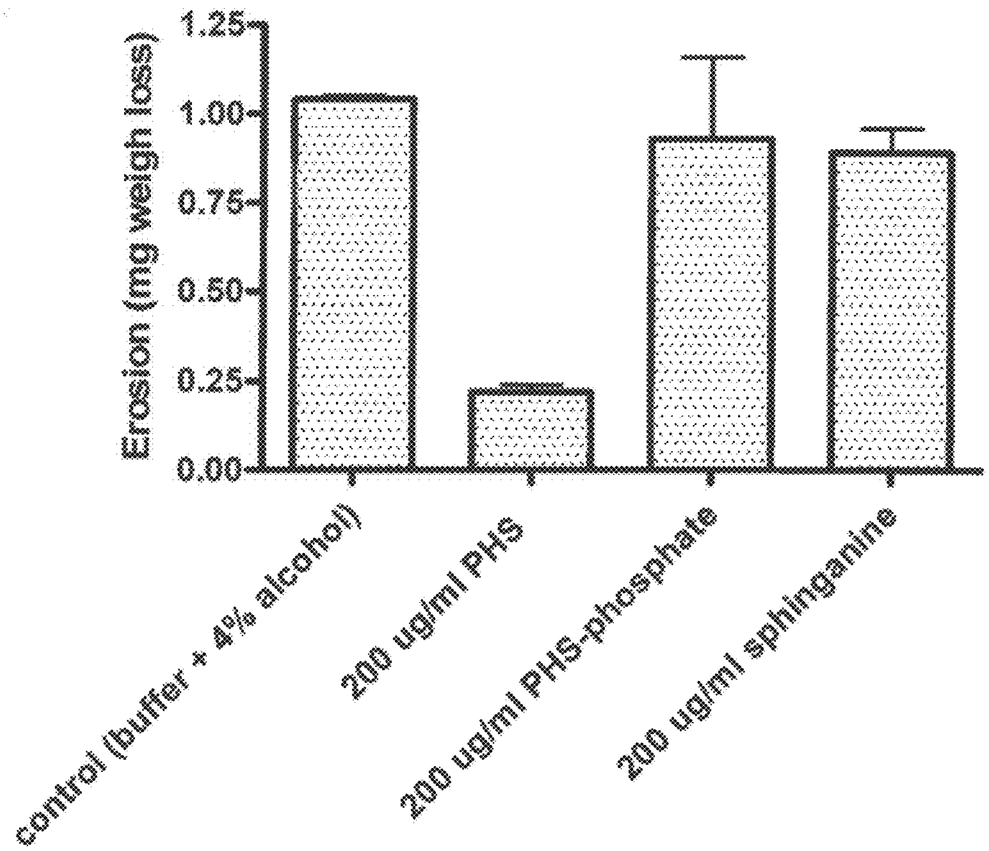

FIG. 7. Effect of phytosphingosine-phosphate, sphinganine, and PHS (phytosphingosine) in saliva buffer.

Figure 8:
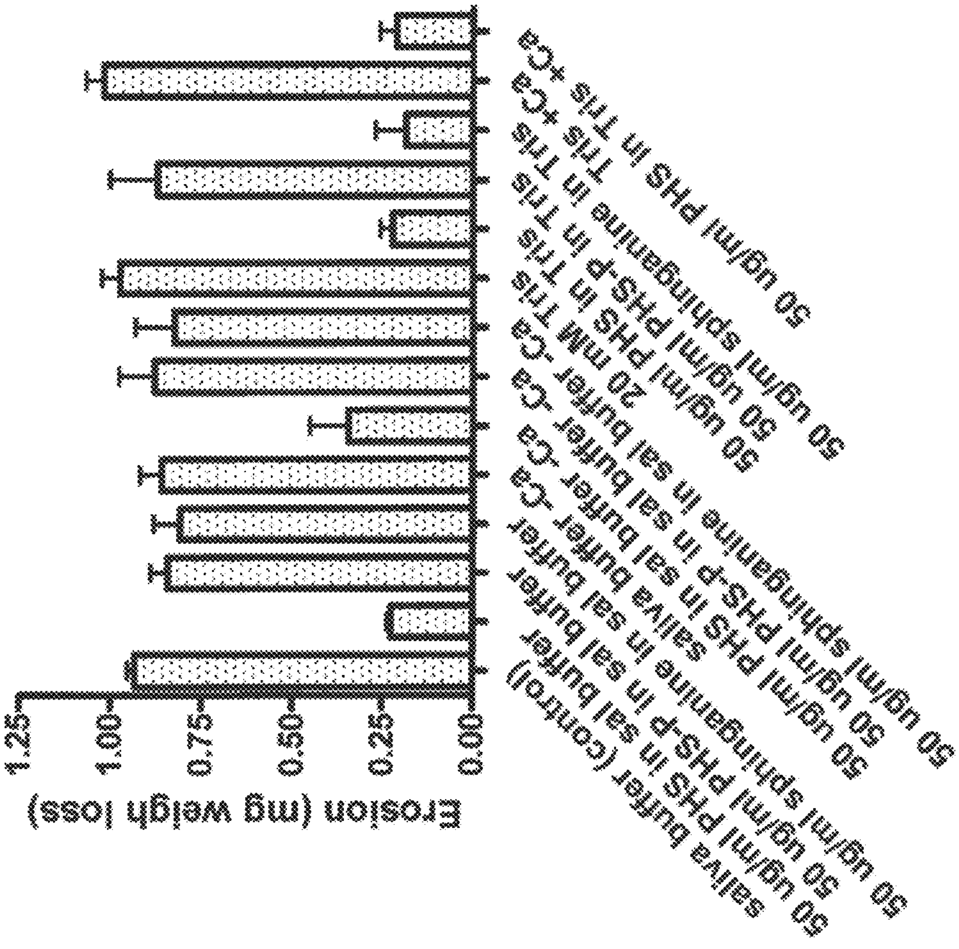

FIG. 8. Effect of buffer on protection by various sphingosines. Discs were treated with the various sphingosines (50 ug/ml in saliva buffer (+/− $CaCl_2$) and 20 mM Tris (+/− $CaCl_2$). Erosion was determined as described in FIG. 7.

Figure 9:
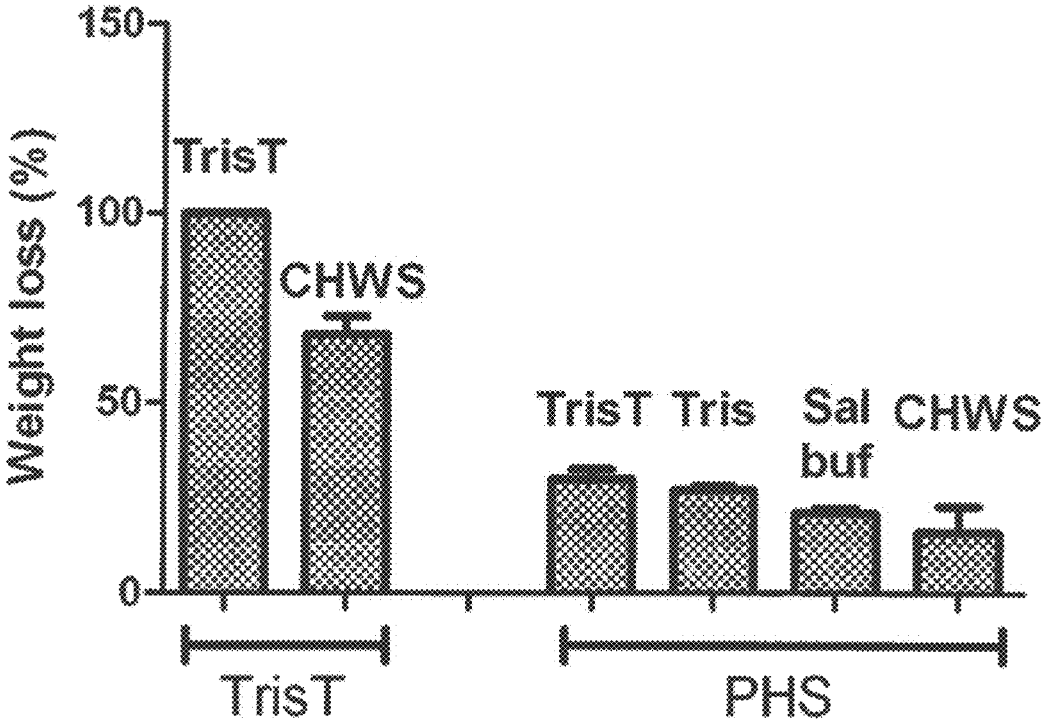

FIG. 9. Protective effect of PHS on saliva coated HAP. HAP disks were incubated with either 20 mM Tris supplemented with 0.1% Tween 20 (TrisT), 20 mM Tris (Tris), saliva buffer (Sal buf) or cleared human whole saliva (CHWS). After 20 hrs disks were rinsed and incubated in either TrisT (left bars, TrisT) or TrisT supplemented with 100 μg/ml PHS (right bars, PHS) for 3 hrs. Disks were rinsed and exposed to 0.1 M citric acid for 30 minutes. After rinsing and drying, disks were weighed to determine the weight loss. Disks covered with a salivary pellicle (CHWS) were protected to the same extent as controls treated with TrisT, Tris or Salbuf.

Figure 10:
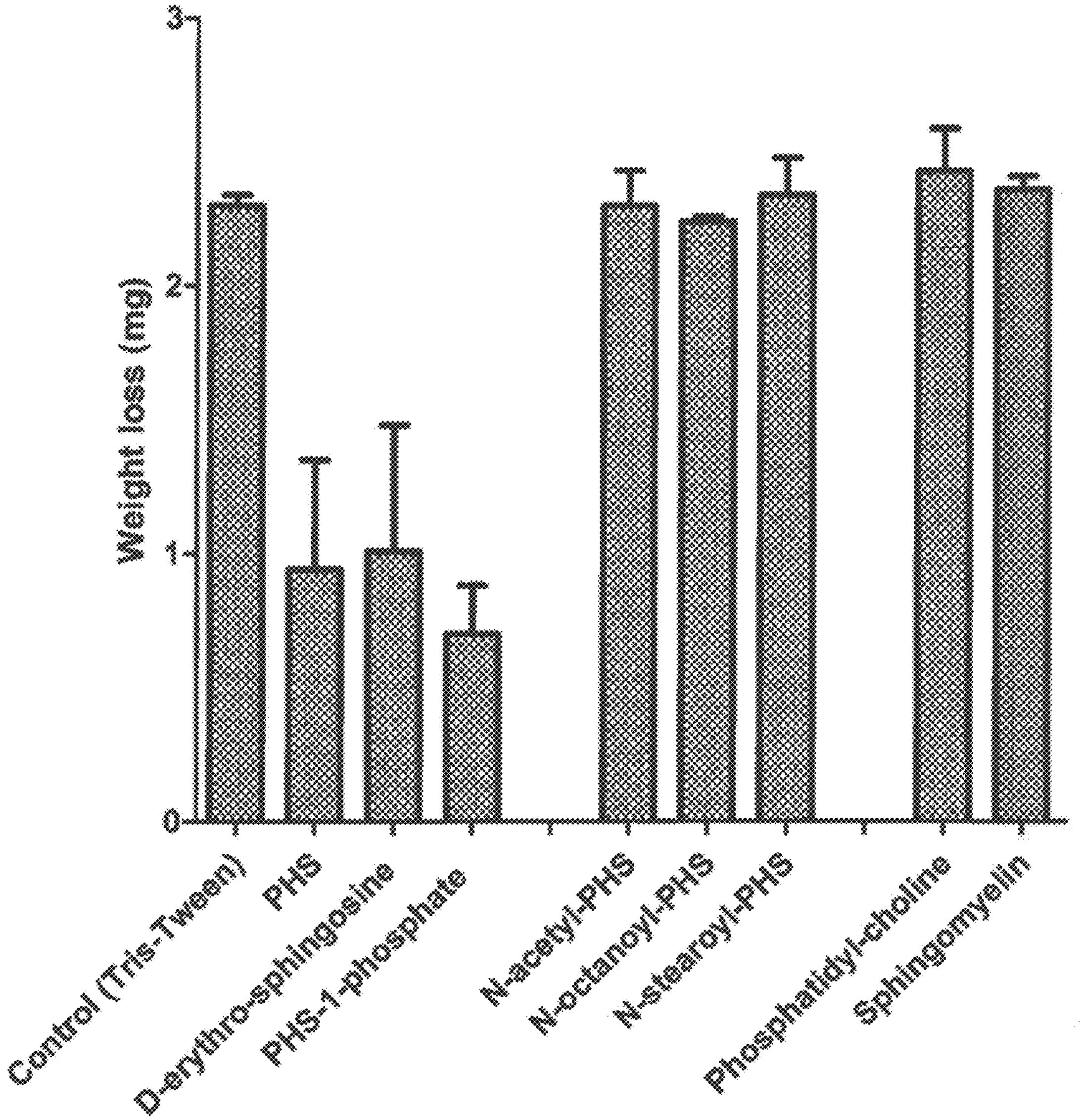

FIG. 10. Anti-erosive effects of different (sphingo)lipids. HAP disks were incubated in triplicate with 100 μg/ml of each lipid in Tris-Tween for 3 hrs. Disks were exposed to 0.1 M citric acid (pH=3.0) for 30 minutes, and weight loss determined.

Figure 11:
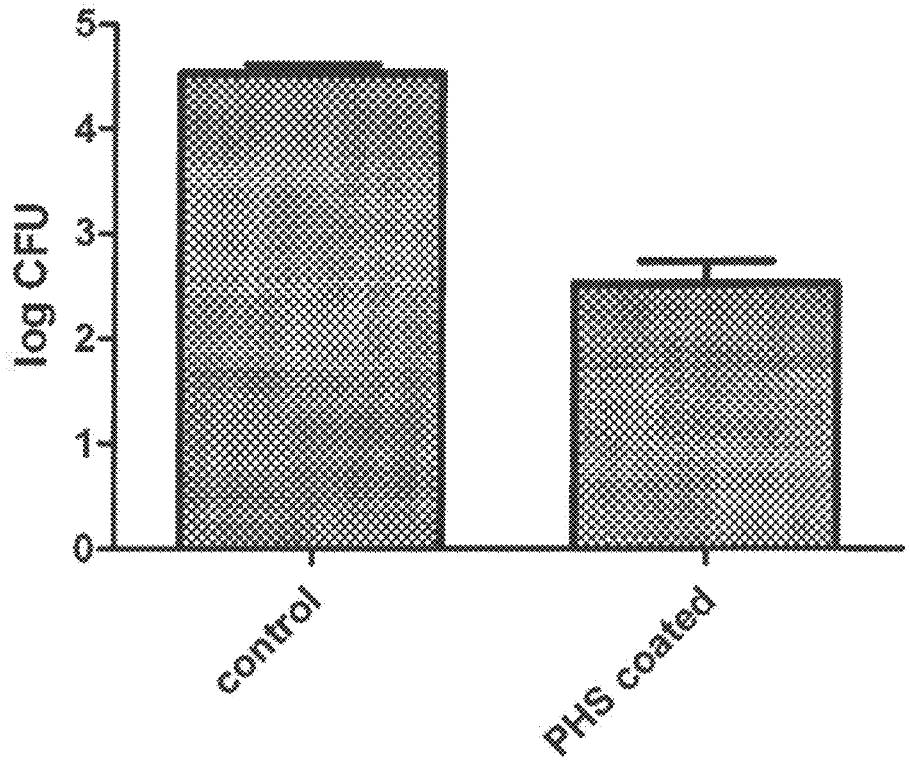

FIG. 11. Anti-adhesive effects of PHS-coating on HAP. Adhesion of bacteria to HAP discs was investigated using an active attachment model. HAP discs were incubated overnight at 30° C. in 20 mM Tris, 0.1% Tween 20, pH 6.8, without (CONTROL) with 100 μg/ml PHS (PHS coated). HAP discs were washed to remove unbound PHS. *Streptococcus mutans* was cultured overnight in BHI medium and diluted 1:10 in half-strength BHI (18.5 g BHI/l, 50 Mm/l PIPES, pH 7.0) to a final density of approximately $10^8$ cells/ml. The lid with the HAP disks was placed on top of the 24 well plate containing 1.5 ml of diluted bacterial suspension and incubated anaerobically for 2 hr at 37° C. The HAP discs were washed twice in cysteine peptone water (CPW), to remove the non-adherent bacteria. The attached layer of bacteria was dispersed by sonification for 2 min with 1 s pulses. The resulting suspension was plated in different dilutions on BHI plates and incubated anaerobically for 48 hr at 37° C. before CFU were counted. PHS inhibited bacterial adhesion for more than 100-fold.

Figure 12:
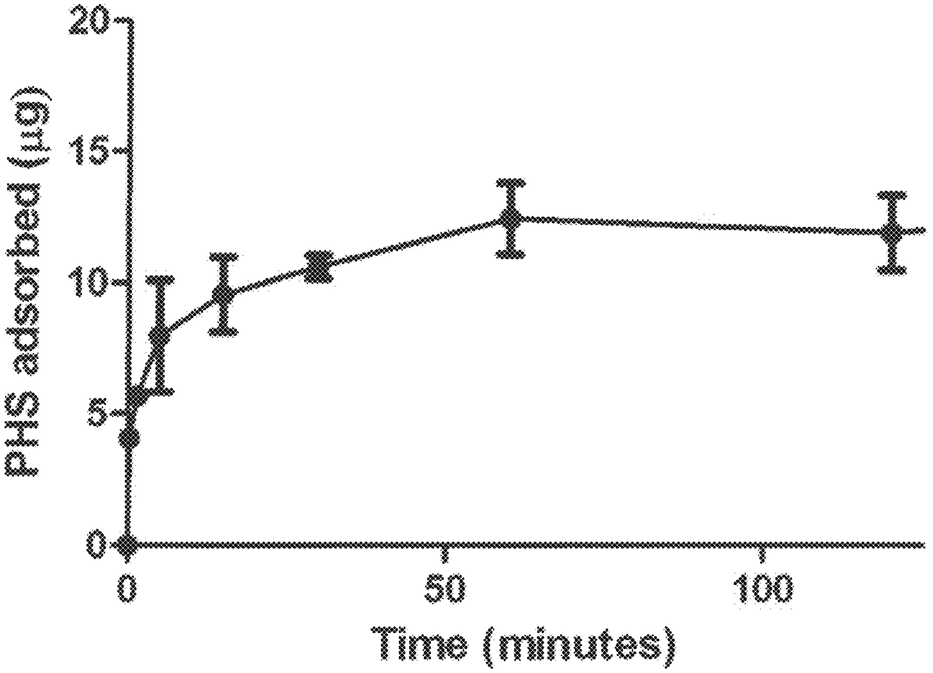

FIG. 12. Time dependency of PHS adsorption to HAP. PHS was mixed with HAP disks and incubated for 0.5, 1.5, 5, 15, 30, 60, 120 and 180 minutes. Disks were rinsed, and adsorbed PHS was extracted with ethanol. After derivatization with OPA, PHS was determined by fluorimetry. Within 5 minutes >65% of the maximal adsorption level was reached.

Figure 13:
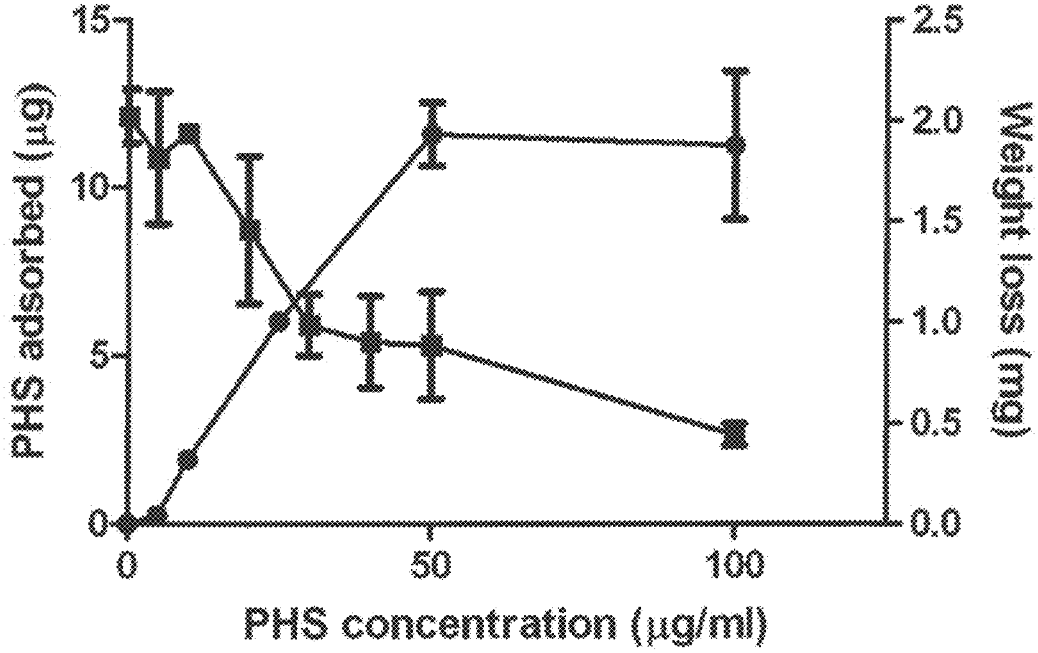

FIG. 13. Adsorption (circles) and protection (squares) as function of PHS concentration. Different concentrations of PHS were incubated with HAP disks for 3 hrs. Amount of adsorbed PHS was determined after extraction and derivatization with OPA using fluorimetry. In a separate experiment PHS treated disks were exposed for 30 minutes to 0.1 M citric acid (pH 3.0) and weight loss determined. Already at submaximal binding levels (approximately 6 μg per disk) PHS maximally protects.

Figure 14:
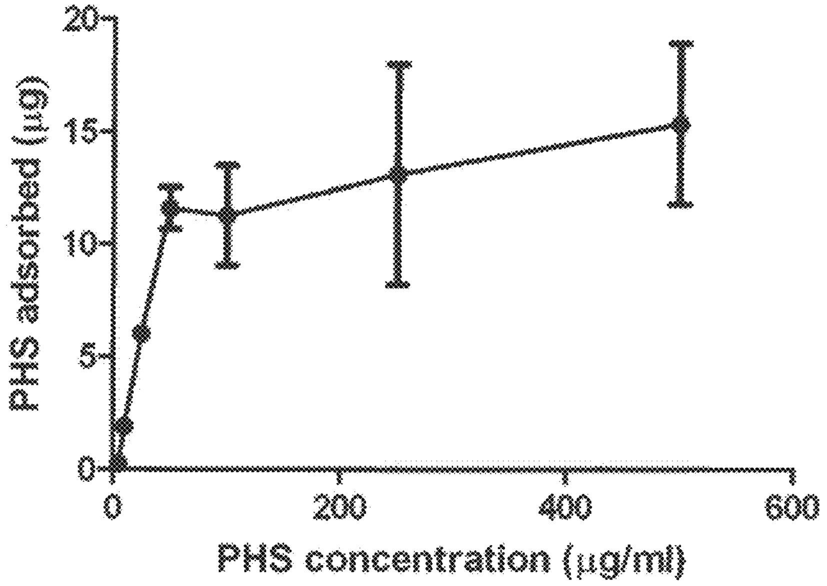
Figure 14:
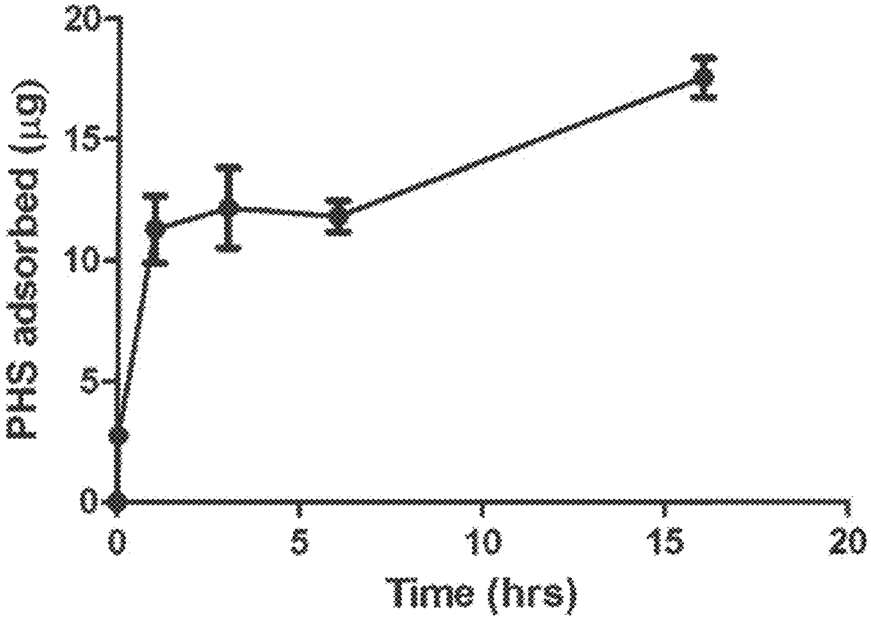

FIG. 14. Binding of PHS to HAP. A. HAP disks were incubated with PHS in varying concentrations. After 3 hrs disks were extracted with methanol, and the amount of PHS adsorbed was determined fluorimetrically. B. HAP disks were incubated with 100 μg/ml PHS. At different time points disks were extracted with methanol and the adsorbed PHS was determined fluorimetrically. Incubations were conducted in triplicate.

Figure 15:
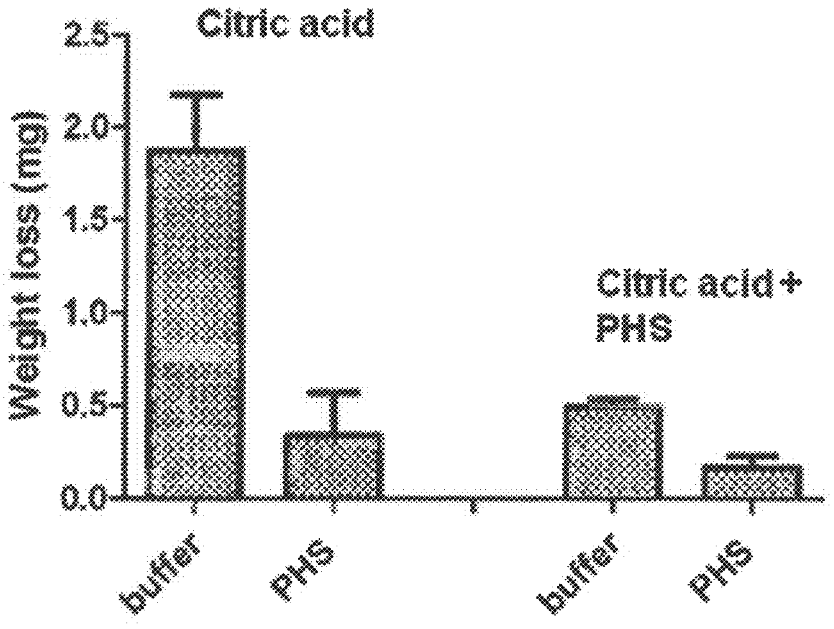

FIG. 15. Protective effects of sphingolipids when present in citric acid during the erosive attack. Left two bars: HA disks are pretreated with buffer or 100 ug/ml PHS for 3 hours followed with a treatment with 0.1 M citric acid (pH=3.0) for 30 minutes. Right two bars: HA disks are pretreated with either buffer or 100 ug/ml PHS and then exposed to 0.1 M citric acid in the presence of 100 ug/ml PHS for 30 minutes.

Figure 16:
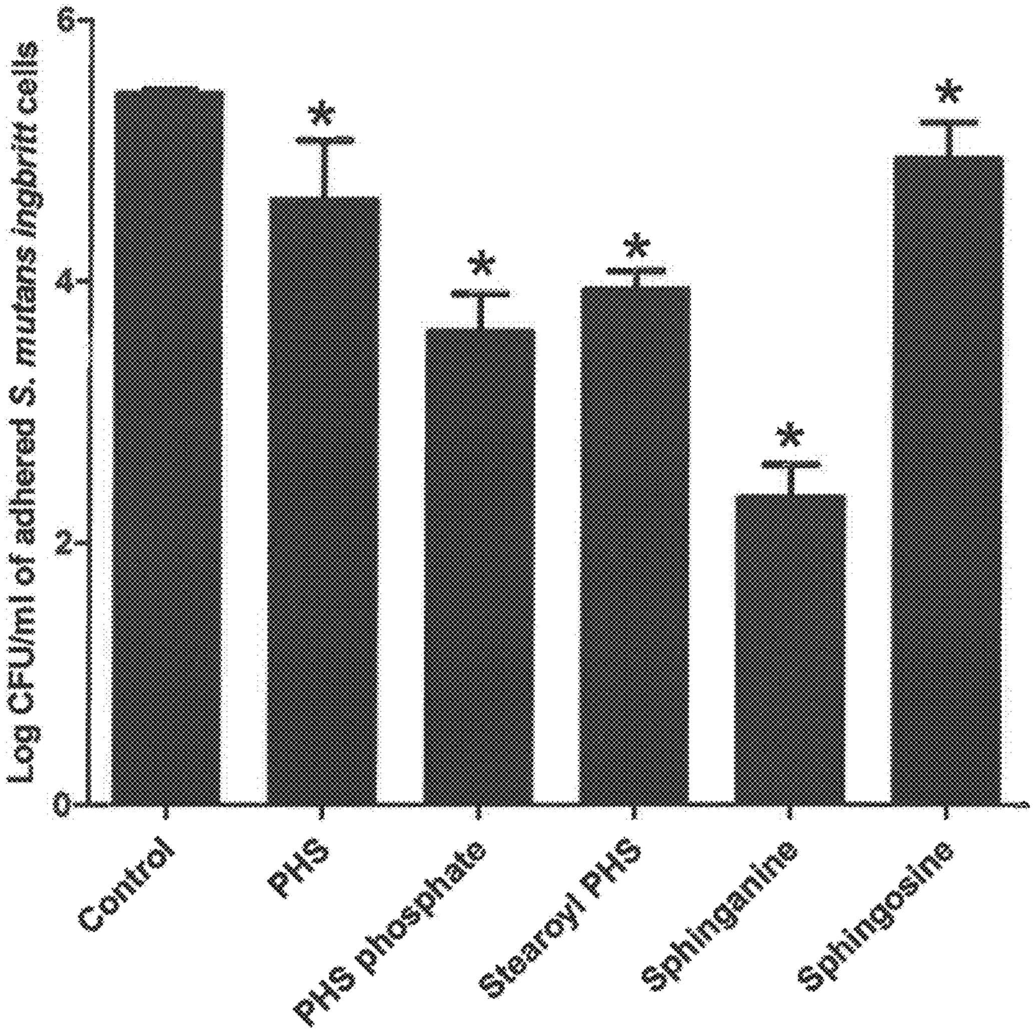

FIG. 16. Antifouling activity of sphingolipids coated on HA discs against *Streptococcus mutans*

Figure 17:
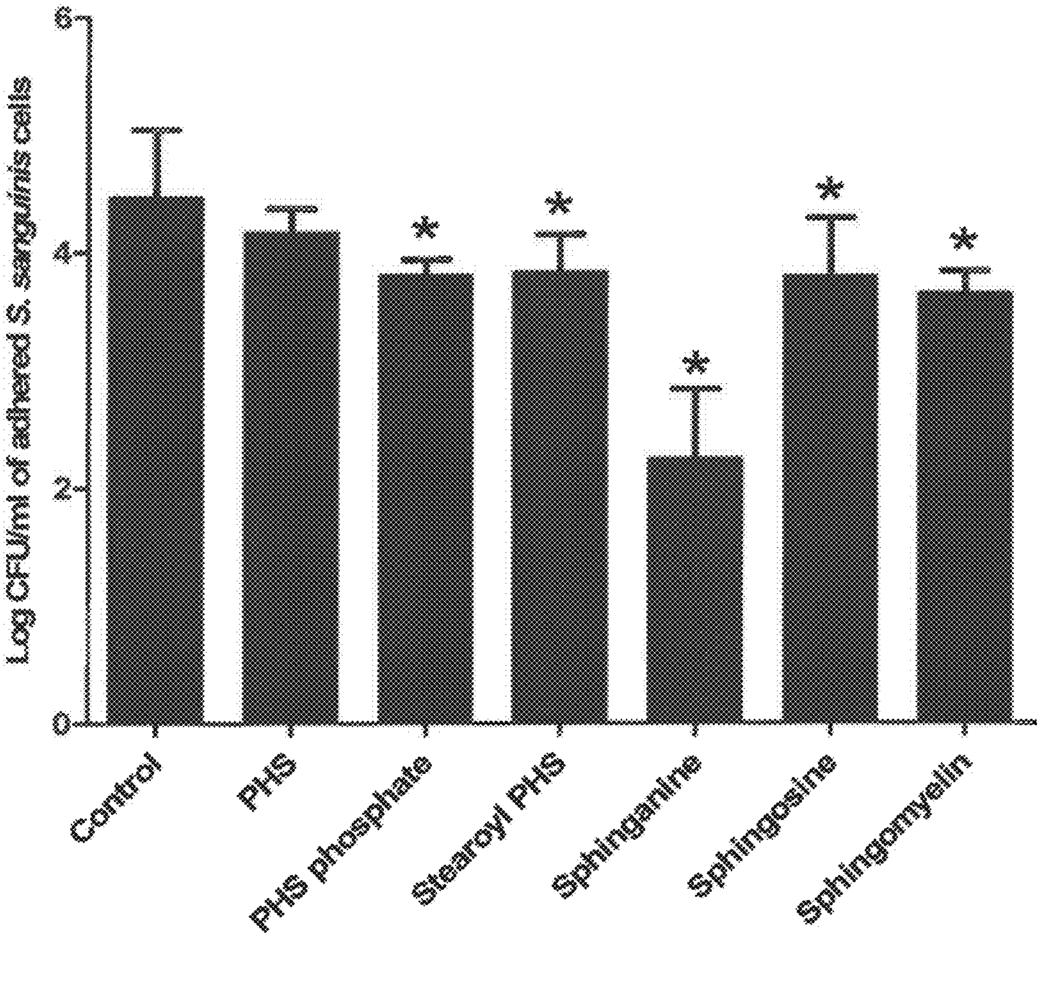

FIG. 17. Antifouling activity of sphingolipids coated on HA discs against *Streptococcus sanguinis*

Figure 18:
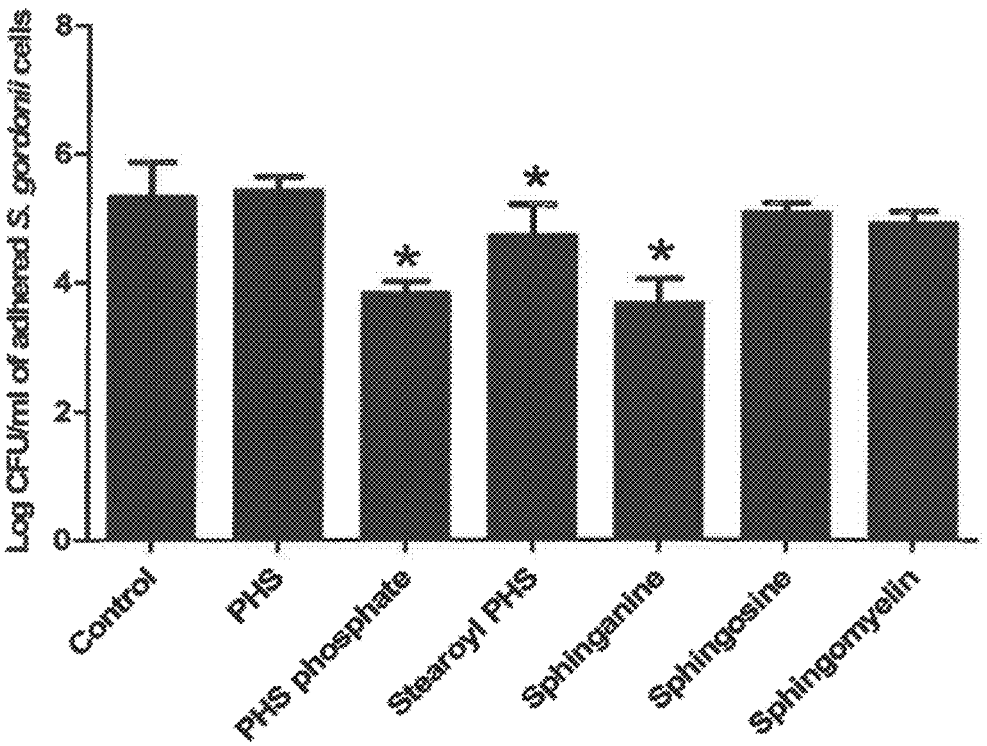

FIG. 18. Antifouling activity of sphingolipids coated on HA discs against *Streptococcus gordonii*

FIG. 19. Exemplary list of non-ionic detergents

DETAILED DESCRIPTION OF THE DISCLOSED EMBODIMENTS

The present disclosure demonstrates the protective effect of surfaces/materials by lipid-containing compounds based on the family of sphingosines. Treatment of hydroxyapatite, the acid-sensitive mineral phase of dental enamel, with a sphingosine compound provided more than 80% protection against dissolution by citric acid relative to untreated samples (see, e.g., FIGS. 1 and 8). Accordingly, methods are provided for protecting hydroxyapatite containing materials using a sphingosine compound. While not wishing to be bound by theory, it is believed that the sphingosine compounds adhere to hydroxyapatite forming a protective barrier. Said adherence renders these compounds useful in the protection against, e.g., acid erosion, biofilm formation, and tooth demineralization.

Preferably, the sphingosine compounds useful in the present disclosure comprise formula I:

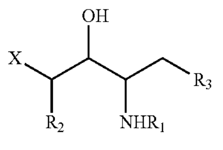

wherein X is a alkyl having 8-24 carbons, preferably 10 to 20 carbons, more preferably a linear alkyl;

$R_1$ is selected from H and $C(=O)C_{1-20}$, preferably $R_1$ is H;

$R_2$ is selected from H, F and OH, preferably $R_2$ is OH; and $R_3$ is selected from OH or F, preferably OH.

Preferably, formula I is

Formula I

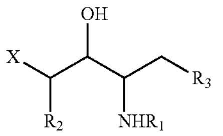

wherein X is an alkyl or alkenyl having 8-24 carbons, preferably 10 to 20 carbons, more preferably a linear alkyl;

$R_1$ is selected from H and $C(=O)C_{1-20}$, preferably $R_1$ is H;

$R_2$ is selected from H and OH, preferably $R_2$ is OH; and $R_3$ is selected from phosphate, OH or F, preferably OH.

Preferably, X is a linear alkyl having 10 to 20 carbons, $R_1$ is H, $R_2$ is OH, and $R_3$ is OH.

More preferably, X is an alkyl or alkenyl having 8-24 carbons, preferably 10 to 20 carbons, more preferably a linear alkyl;

$R_1$ is H;

$R_2$ is selected from H and OH, preferably $R_2$ is OH; and $R_3$ is selected from phosphate, OH or F, preferably OH.

Preferably formula I is:

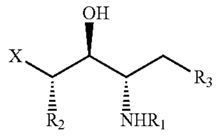

Preferably, the sphingosine compound is a phytosphingosine-based compound. Such compounds include N-tetracosanoyl phytosphingosine, N-stearoyl phytosphingosine, N-oleoyl phytsosphingosine, N-linoleoyl-phytosphingosine, N-(2-hydroxytetracosanoy-1), phytosphingosine, N-(2-hydroxyoctdecanoyl) phytosphingosine, N-phytosphingosine, 22(2hydroxyoctdecanoyl) hydroxyoctdecanoyl) phytosphingosine, N-(27-stearoyloxy-hepatoaconsanoyl) phtosphingosine, N_(27-oleoyloxheptacosanoyl)phytosphingosine, N (27-linoleoyoxyheptaconsa-noyl) phytosphingosine, N-(23-stearoyloxytricosanoyl) phytosphingosine, N-acetyl-phytosphingosine, N-hexadecanoyl-phytosphingosine, N-hexanoyl-phytosphingosine, N-octadecanoyl-phytosphingosine, and N-octanoyl-phytosphingosine maybe used. In preferred embodiments, the sphingosine compound is a sphingolipid comprising a sphingoid base as described herein. The most preferred sphingosine compound is phytosphingosine. Also preferred compounds are phytosphingosine-phosphate and D-erythro-sphingosines, such as D-erythro-sphingosine C15.

Additionally, the present disclosure demonstrates that sphingosine compounds can prevent bacterial adherence to a surface. This makes them useful as agents to reduce or prevent biofilm formation. Such compounds can be used, e.g., as coatings on medical devices and surgical equipment. This effect also increases their usefulness in oral care and food compositions. The effect of the sphingosine compounds preventing bacterial adherence is separable from any effect as a bactericide. In the methods and compositions (e.g., oral care and food compositions) described herein, the sphingosine compounds are not used as antimicrobials but rather to prevent bacterial adherence. Preferably, for these applications and compositions the sphingosine compound is selected from one or more of the following: PHS, PHS phosphate, stearoyl PHS, sphinganine, and sphingosine. Most preferred for the prevention of bacterial adherence is sphinganine. Preferably, more than one sphingosine compound is used in the methods and compositions as described herein. Preferably, PHS and sphinganine are used together in a method, composition, or coated on an article as described herein. Preferably the adherence of oral bacteria is reduced. Preferably the adherence of *S. gordonii* is reduced. Preferably the adherence of *S. sanguinis* is reduced. More preferably, the adherence of *S. mutans* is reduced.

The sphingosine compound may also be a conjugate of said compound, such as a sphingolipid. Sphingolipids comprise a complex range of lipids in which fatty acids are linked via amide bonds to a long-chain base or sphingoid. More precisely, sphingolipids consist of long-chain bases, linked by an amide bond to a fatty acid and via the terminal hydroxyl group to complex carbohydrate or phosphorus-containing moieties. Sphingoid bases include dihydrosphingosine (sphinganine), sphingosine, and phytosphingosine. Ceramides are a specific group of sphingolipids containing sphingosine, phytosphingosine or dihydrosphingosine as a base in amide linkage with a fatty acid. Sphingolipids suitable for the present invention have a sphingoid base having the formula of formula I as disclosed herein.

Suitable conjugates of sphingosine compounds also comprise the compounds of formula I conjugated to a protein or peptide moiety. Said moiety may improve the production, delivery, HAP targeting, stability, or efficacy of the sphingosine compound. Preferred peptide moieties are HAP binding moieties. A number of such peptides are known in the art including statherin, salivary agglutinin, polyglutamate, and casein peptides. Preferably, said peptide comprises the sequence DSpSpEEK (from statherin, wherein Sp is phorphorylated serine) or the HAP binding domain of salivary agglutinin.

Conjugation of sphingosine compounds to proteins and peptides is well-known in the art and is described, e.g., in U.S. Pat. No. 5,543,390, which is hereby incorporated by reference.

One aspect of the disclosure provides the use of a sphingosine compound for coating bone or tooth. The sphingosine compound acts as a protective barrier against, e.g., acid erosion and the formation of salt precipitation leading to tartar.

One aspect of the disclosure provides the use of a sphingosine compound for coating of phosphate- and sulphate containing materials. One aspect of the disclosure provides the use of a sphingosine compound for coating surfaces comprising hydroxyapatite, plastic, glass, silicone, fluorapatite, silicate, and surfaces containing titanium, carbonate- (such as calcium carbonate), phosphate- (such as calcium phosphate) and/or sulphate- (such as calcium sulphate) groups. The sphingosine compound acts as a protective barrier against, e.g., acid erosion by acidic liquids and gases One aspect of the disclosure provides the use of a sphingosine compound for preventing or reducing tooth demineralisation. Tooth enamel naturally undergoes a process of demineralization, which is increased by the presence of acid, e.g., from food, drinks, gastric acid, or produced by bacteria. Tooth demineralisation is the underlying process involved in the development of dental caries, dental erosion and dentine hypersensitivity (herein referred to as tooth demineralisation disorders). Preferably, said tooth demineralization disorder is due to the presence of acid which has not been produced by bacteria, e.g., the disorder is from acidic food, acidic beverages, or gastric acid. Preferably, said sphingosine compounds are used in methods for the preventing or treating tooth demineralisation disorders resulting from the consumption of acidic food or beverage or from gastric acid.

Hydroxyapatite becomes soluble when exposed to acidic environments. Salts, such as calcium-phosphate salts, may also precipitate on hydroxyapatite. Accordingly, methods are provided for protecting a hydroxyapatite surface comprising contacting said surface with a sphingosine compound as described herein. In some embodiments, the surfaces are pretreated with the sphingosine compound. In some embodiments, the sphingosine compound is present in an acidic composition (e.g., in a carbonated beverage). The methods are especially useful for protecting hydroxyapatite containing materials from acid erosion and from the accumulation of precipitated salts. Hydroxyapatite surfaces include natural and prosthetic teeth and well and natural and prosthetic bone.

In preferred embodiments of the methods and products described herein, a sphingosine compound is used together with hydroxyapatite (nano) particles. Hydroxyapatite adheres to the surfaces of teeth and promotes their recalcification and strengthening. It has been successfully used in a dental fine filling method for protecting and restoring pits, fissures and lesions in enamel. Hydroxyapatite has been used in toothpastes in Japan since 1980 and is commercially available under such names as, e.g., Apagard® nHAP toothpaste, Sangi Co., Japan, which provides 5% and 10% hydroxyapatite nanoparticle containing toothpaste.

The average particle diameter of the hydroxyapatite particles is preferably in the range from 1 to 200 nm, more preferably from 5-100 nm. The basic building blocks of enamel are usually 20-40 nm of HAP. Preferably, the hydroxyapatite particles used herein have an average particle diameter of between 15-50 nm. Most preferred are those have an average particle diameter of around 20 nm as described in Li et al. (J of Mater. Chem 2008 18, 4079-4084).

The hydroxyapatite nanoparticles may be provided coated with one or more sphingosine compound as described herein. Such pre-coated particles may be used in oral care compositions or as coating for prostheses, e.g., prosthetic tooth.

In dental caries, acidic end products of anaerobic bacterial metabolism in the dental plaque cause local dissolution of dental enamel, typically at sites which are difficultly accessible for dental hygiene. Dental caries include arrested dental caries, incipient dental caries, pit and fissure cavity, primary dental caries, secondary dental caries, smooth surface cavity. In some embodiments, the tooth demineralization disorder is not dental caries. Dental erosion is the chemical dissolution of dental surfaces by acids from dietary or gastric origin. Dentine hypersensitivity is the pain or discomfort arising from exposed dentine. In preferred embodiments, the compounds described herein are useful for preventing, treating or reducing acid erosion of the teeth, i.e., dental erosion. See US Patent Application No. 20100034750 for a discussion of the development of dental caries and erosion following demineralisation.

Tooth demineralization and tartar formation can be reduced or prevented by the application of a sphingosine compound as described herein.

Remineralization is a natural process resulting in the return of minerals to the tooth surface. The reduction or prevention of tooth demineralization, as used herein, refers to the slowing of the demineralization process such that the net effect of demineralization/mineralization process is such that demineralization is reduced or prevented. Use of a sphingosine compound or composition comprising said sphingosine compound as described herein reduces the net effect of demineralization by at least 5, at least 10, at least 20, at least 30, at least 50, at least 60, or at least 80% in comparison to controls. Use of a sphingosine compound or composition comprising said sphingosine compound as described herein also reduces the formation of tartar by least 5, at least 10, at least 20, at least 30, at least 50, at least 60, or at least 80% in comparison to controls.

The sphingosine compounds are also useful in the treatment or prevention of xerostomia. Xerostomia, also known as dry mouth, refers to the lack of saliva and can be caused by insufficient production of saliva. It may be a symptom of an underlying disease such as diabetes and auto-immune disorders or a side-effect of medication. It is also associated with old age, bodily dehydration, and anxiety. Although the sphingosine compounds may be provided in any composition disclosed herein, they are preferably provided in a chewing gum or artificial saliva product for this indication.

The sphingosine compound may be used in a subject suffering from or at risk of suffering from, dental erosion, dental caries, tartar formation, dentine hypersensitivity, and xerostomia. The compound may reduce or prevent said disorders or alleviate a symptom thereof. Alternatively, the compound may be used prophylactically to prevent the risk of developing such a condition or to strengthen the teeth by reducing demineralization.

The sphingosine compounds may be provided in any number of suitable compositions including a pharmaceutical composition, an oral care composition, and food compositions. Preferably, said composition comprises, in particular when phytosphingosine-phosphate is used, a non-ionic, neutral detergent, such as Tween 80, Triton X-100, Triton X114, Brij 35, Brij 58, Nonidet P40, octylglycoside and ethoxylated stearyl alcohol.

X114, Brij 35, Brij 58, Nonidet P40, octylglycoside and ethoxylated stearyl alcohol, and any non-ionic detergent as listed in FIG. 19 are compatible.

Preferably, the sphingosine compound is provided in the form of an oral care composition as described herein. The dental enamel of a tooth surface is contacted with said compound or composition by, for example, brushing the teeth with a dentifrice (such as toothpaste or tooth powder), rinsing with a dentifrice slurry or mouthrinse, or chewing a gum product. Other methods include contacting the topical oral gel, mouthspray, or other form such as strips or films with the subject's teeth and oral mucosa. The compound or composition may be applied directly to the teeth, gums, or other oral surface with a brush, a pen applicator, or with the fingers. Sphingosine compounds may also be provided in a food product. Food products include products for human and/or animal consumption and include both solid and liquid (beverage) products. Preferably, the sphingosine compound is selected from one or more of the following: PHS, PHS phosphate, stearoyl PHS, sphinganine, and sphingosine. Preferable the composition includes PHS and at least one additional sphingosine compound, preferably selected from PHS phosphate, stearoyl PHS, sphinganine, and sphingosine. Preferably the composition comprises PHS and sphinganine.

The sphingosine compounds and compositions comprising said compounds are also useful in cosmetic applications.

The sphingosine compounds and compositions comprising said compounds are useful in both therapeutic applications (e.g., prevention and reduction of tooth caries) and non-therapeutic applications (e.g., cosmetic treatments which reduce tooth discoloration).

As used herein, "tooth" refers to a natural tooth as well as hydroxyapatite containing prosthetic teeth, including an inlay, a crown, dentures, and tooth implants.

The sphingosine compounds may be used in any animal in need thereof, including livestock, household pets or other domestic animals, or animals kept in captivity. Pet care products such as chews and toys may be formulated to contain the present oral compositions. Preferably, the compounds are used in humans.

The sphingosine compound is preferably provided to the teeth at least once per day, more preferably twice per day, e.g., once in the morning and once in the evening. Preferably, the sphingosine compound is provided to the teeth regularly, or rather on a daily (or twice daily) basis, over the course of several days, weeks, or months.

Preferably, the sphingosine compound is provided in an oral care composition. Such compositions must therefore be suitable for use in humans and animals. As used herein, oral care compositions are retained in the oral cavity for a time sufficient to contact the teeth and are not intentionally swallowed for purposes of systemic administration. Preferred oral care compositions include toothpaste, dentifrice, tooth powder, tooth gel, subgingival gel, mouthrinse, artificial saliva, denture product, mouthspray, lozenge, oral tablet, or chewing gum. Sphingosine compounds may also be incorporated onto strips or films for direct application or attachment to oral surfaces. Some sphingosine compounds are more effective when provided in a buffer not containing, or containing a minimal amount of, phosphate (e.g., sphinganine in FIG. 8). The efficacy of these compounds may be improved by providing them in oral care compositions lacking phosphate (or comprising only minimal amounts). Alternatively, or in addition to, such compounds may be provided in a product that does not rely on saliva. For example, a denture product which treats dentures outside the mouth (such as when placed in a cup) would have no or minimal contact with saliva.

Preferably, the sphingosine compound is present in the oral care composition at a concentration of more than 5 ug/ml, preferably at least 10 ug/ml, more preferably at least 20 ug/ml, more preferably at least 50 ug/ml and most preferred at least 100 ug/ml. Preferably, PHS is present at a concentration of at least 20 ug/ml. In the case of a solid oral care composition the sphingosine compound is present at a concentration of more than 2.5 μg/gram.

Preferably the oral care composition further comprises hydroxyapatite particles as described herein. Preferably, the composition comprises between 0.001-50 wt. %, more preferably between 2-20 wt. % of said particles. Hydroxyapatite nanoparticles are commercially available from, e.g., nanoXIM•CarePaste (Fluidinova, SA). The hydroxyapatite particles may be precoated with sphingosine compound. Such pre-coating may reduce the amounts of sphingosine compound needed to have an effect.

The composition and means for preparing suitable oral care compositions are well-known in the art. In some embodiments, the products are in the form of dentifrices, such as toothpastes, tooth gels and tooth powders. A skilled person can select the appropriate components of the oral care composition based on the particular sphingosine compound used.

Components of such toothpaste and tooth gels generally include one or more of a dental abrasive (from 5% to 50%), a surfactant (from 0.5% to 10%), a thickening agent (from 0.1% to 5%), a humectant (from 10% to 55%), a flavoring agent (from 0.04% to 2%), a sweetening agent (from 0.1% to 3%), a coloring agent (from 0.01% to 0.5%) and water (from 2% to 45%) as well as an anticaries agent (from 0.05% to 0.3% as fluoride ion) and preservatives. Tooth powders, of course, contain substantially all non-liquid components.

Suitable components of the toothpaste disclosed herein include Carbomer 956, a polymer used for thickening and as an emulsion stabilizer; Carrageenan, a thickening agent; Carboxymethylcellulose sodium, also known as cellulose gum, is used as a thickener; Cocamidopropyl betaine, a foaming ingredient derived from coconut oil; D&C Yellow #10, FD&C Blue #1, and D&C Red #30, Synthetic dyes; Glycerin, to balance and maintain moisture levels; Hydrated silica, an abrasive; Mica, a mild abrasive to aid in polishing of the tooth surface; PEG-8 and PEG-12, humectants and solvents; Poloxamer 407, a surfactant; Propylene glycol, a humectant; PVM/MA Copolymer, a binder; Sodium benzoate, prevents the buildup of micro-organisms in the toothpaste; Sodium fluoride, strengthens enamel, prevents cavities and fights plaque; Sodium hydroxide, to neutralize the pH of other ingredients; Sodium saccharin; artificial sweetener; Sorbitol, a sugar alcohol and a humectant and texturizing agent; Titanium dioxide, it gives non-gel toothpastes their bright whiteness; Triclosan, to fight gingivitis; and Xanthan gum, a viscosity agent.

In a preferred embodiment, the disclosure provides a toothpaste comprising a dental abrasive, a surfactant, a thickening agent, a humectant, and a sphingosine compound as described herein.

Suitable dental abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

The most common surfactant currently used in toothpastes is sodium dodecyl sulfate (SDS). We have found that SDS greatly reduces the protective effects of the sphingosine compounds. Therefore, SDS should preferably not be used in the oral care compositions, in particular when phytosphingosine is the sphingosine compound. SDS-free toothpastes are commercially available, in which, e.g., glycyrrhizin (Tom's of Maine Clean & Gentle Care Toothpaste™) or Sodium Lauroyl Sarcosinate (Dr. Katz PerioTherapy Treatment Gel™) is substituted for SDS. More preferably, the oral care composition is free of SDS, SLS, and glycyrrhizin. Preferably, the surfactant is a non-ionic detergent such as Tween 20 (polyoxyethylene sorbitan monolaurate), Triton X-100, Tween 80, and other Tween detergents. Additional non-ionic detergents are listed in 19. Preferably, the oral composition does not contain an ionic detergent.

Suitable thickening agents include carboxyvinyl polymers, carrageenan, hydroxyethyl cellulose, laponite and water soluble salts of cellulose ethers such as sodium carboxymethylcellulose and sodium carboxymethyl hydroxyethyl cellulose, polyethyleneoxide, vora hyaluronic acid glucan, gum karaya, xanthan gum, and gum Arabic.

Suitable humectants include edible polyhydric alcohols such as glycerin, sorbitol, xylitol, butylene glycol, polyethylene glycol, and propylene glycol, especially sorbitol and glycerine.

Suitable flavoring agents include oil of wintergreen, oil of peppermint, oil of spearmint, clove bud oil, menthol, anethole, methyl salicylate, eucalyptol, cassia, 1-menthyl acetate, sage, and eugenol.

An exemplary mouthwash composition includes e.g., ethanol (about 10% and about 20% by weight), propylene glycol (about 5% and about 15% by weight), glycerol (about 5% and about 20% by weight) and in lessor amounts, flavouring and coloring agents.

The active ingredients of mouthwash compositions are usually alcohol, chlorhexidine gluconate, cetylpyridinium chloride, hexetidine, benzoic acid (acts as a buffer), methyl salicylate, benzalkonium chloride, methylparaben, hydrogen peroxide, domiphen bromide and sometimes fluoride, enzymes, and calcium. They can also include essential oils that have some antibacterial properties, like phenol, thymol, eugenol, eucalyptol] or menthol. Ingredients also include water, sweeteners such as sorbitol, sucralose, sodium saccharin, and xylitol (which doubles as a bacterial inhibitor). As described above, it is preferred that a non-ionic surfactant is included in the mouthwash.

Chewing gum compositions typically include one or more of a gum base (from 50% to 99%), a flavoring agent (from 0.4% to 2%) and a sweetening agent (from 0.01% to 20%). Lozenges include breath mints, troches, pastilles, microcapsules, and compressed tablets.

Artificial saliva, also known as a saliva substitute such as Oralube™, is a solution which simulates saliva. Artificial saliva normally contains water and electrolytes (e.g., potassium, sodium, calcium, chloride, phosphate) and may also contain enzymes, cellulose derivatives, and flavouring agents. Suitable formulations are known in the art and are described, e.g., in U.S. Pat. Nos. 5,541,165 and 5,128,132, which are hereby incorporated by reference in their entirety.

Preferably, the sphingosine compound is provided in a food product supplemented with said compound. Suitable food products include dairy products, processed food products, oils, food and/or vitamin supplements, snack products, and beverage products (such as, sport drinks).

Preferably, the sphingosine compound is provided in beverages supplemented with the said compound. Suitable beverages include water, alcoholic drinks (such as beer, wine), soft drinks (such as cola, iced tea, lemonade, fruit punch, sparkling water), fruit juices (such as orange juice, tangerine juice, grapefruit juice, pineapple juice, applejuice, grapejuice, lime, and lemon juice), vegetable juice (such as carrot drink and tomato drink), hot drinks (such as coffee based beverages, tea, hot chocolate, gluhwein,). Preferably, the sphingosine compound is provided in an acidic food composition, preferably said food composition has a pH of less than 7, less than 6, or preferably less than 5. The pH of soda pop is around 3.

Food products also include animal chow (e.g., dog foods, cat foods) and supplements (e.g., biscuits, chews). Such products are well-known in the art and are described, e.g., in U.S. Pat. Nos. 5,405,836; 6,379,725 and U.S. patent application Publication Nos. 2002/0119241 and 20050123585, all of which are hereby incorporated by reference in their entirety.

Preferably, the sphingosine compound is present in the food product at a concentration of more than 5 ug/ml, preferably at least 10 ug/ml, more preferably at least 20 ug/ml, more preferably at least 50 ug/ml and most preferred at least 100 ug/ml. In the case of a solid food product the sphingosine compound is present at a concentration of at least 1 μg/gram, at least 2.5 μg/gram, at least 5 μg/gram, or at least 100 μg/gram.

Sphingosine compounds are also useful for preventing or reducing the adhesion of bacteria to a surface. In particular, these compounds are useful in the prevention or reduction of biofilm formation. Biofilms typically contain millions of tightly-packed bacterial cells encased in a polymeric matrix attached to a surface. Biofilms cause corrosion and biofouling of industrial equipment and chronic infections in clinical settings.

In one aspect, a method is provided for preventing or reducing the adhesion of bacteria to a surface and/or preventing or reducing biofilm formation on a surface, comprising treating said surface with a sphingosine compound as described herein. This effect of sphingosine compounds is different from the reported anti-microbial properties of sphingosine compounds in US Publication 20110045073, where a number of sphingosine compounds were used to potentiate the antimicrobial effect of salivary antimicrobial peptides.

Preferably, the methods comprising treating a medical device or surgical instrument with a sphingosine compound. Preferably, said medical device is a device which is to be inserted or implanted into a human or animal body, preferably for a period of several hours or longer. Medical devices include, e.g., prosthetics (hip implants, dental implants, prosthetic joint, a voice prosthetic, a penile prosthetic) a mechanical heart valve, a cardiac pacemaker, an arteriovenous shunt, a schleral buckle, catheters (e.g., central venous catheter, an intravascular catheter, an urinary catheter, a Hickman catheter, a peritoneal dialysis catheter, an endrotracheal catheter), tympanostomy tube, a tracheostomy tube, a surgical suture, a bone anchor, a bone screw, an intraocular lens, a contact lens, an intrauterine device, an aortofemoral graft, or a vascular graft. Surgical instruments include, e.g., clamp, forceps, scissor, skin hook, tubing, needle, retractor, scaler, drill, chisel, rasp, or saw.

The disclosure also provides medical devices at least partially coated with a sphingosine compound as disclosed herein. The articles to be treated with the sphingosine compounds may be sprayed with or soaked in solutions comprising said compounds. It is within the purview of a skilled person to process such articles, in particular medical devices.

The sphingosine compounds can be used to coat various materials including polysterene, polyethylene, silicon, glass, ceramics, glass-cement ionomer, and polymethyl methacrylate (bone cement). Said compounds are also useful for coating phosphate or sulphate containing materials.

Definitions

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

The invention is further explained in the following examples. These examples do not limit the scope of the invention, but merely serve to clarify the invention.

REFERENCES

Anderson P, Bollet-Quivogne F R G, Dowker S E P, Elliott J C. Demineralization in enamel and hydroxyapatite aggregates at increasing ionic strengths. Arch Oral Biol 2004; 49:199-207.

Jensdottir T, Arnadottir I B, Thorsdottir I, et al. Relationship between dental erosion, soft drink consumption, and gastroesophageal reflux among Icelanders. Clin Oral Investig 2004; 8:91-96.

Veerman ECI, Valentijn-Benz M, van 't Hof W, Nazmi K, van Marle J, Nieuw Amerongen AV. Phytosphingosine kills Candida albicans by disrupting its cell membrane. Biol. Chem 2010; 391:65-71.

Navazesh M, Mulligan R A, Kipnis V, Denny P A, Denny P C. Comparison of whole saliva flow rates and mucin concentration in healthy Caucasian young and aged adults. J Dent Res; 1992; 71:1275-1278.

EXAMPLES

Determination of Protective Effects of Phytosphingosine

Dental enamel consists largely of hydroxyapatite crystals $(Ca_{10}(PO_4)_6(OH)_2$. Sintered at high temperatures, hydroxyapatite discs can be produced with physical characteristics (e.g. hardness and density) resembling those of enamel (Anderson et al, 2004), which can be used to determine erosive properties of solutions (Jensdottir et al, 2005) by measuring weight loss from hydroxyapatite after immersion in an erosive (acidic) solution.

Hydroxyapatite discs, sintered at 1250° C. and with a relative density of 98% were obtained from Swerea, Stockholm, Sweden. The lateral and bottom surfaces of the discs were covered with nail polish so that one side remained uncoated. Next, discs were cleaned by sanding with sand paper (3M734 P600) rinsed with demineralised water, dried at 37° C. overnight and weighed to determine the initial mass. Hydroxyapatite discs were placed in the wells of 12 well cell culture plates (Greiner bio-one, Frickenhausen, Germany), to which was added 1.5 ml of phytosphingosine (PHS in various concentrations dissolved in saliva buffer (2 mM potassium phosphate, 50 mM KCl, 1 mM $CaCl_2$, 0.1 mM $MgCl_2$, pH 6.8) under gently shaking for 3 hours at 37° C. After three times rinsing with 4 ml saliva buffer to remove unbound PHS, discs were placed in new wells with 4 ml of 0.1 M citric acid (pH=3.0). After 30 minutes citric acid was pipetted off and discs were rinsed 3 times with 4 ml demineralized water, dried overnight at 37° C. and weighted. The difference in weight before and after the erosive treatment was taken as a measure for erosion. The experiments were conducted in triplicate and were repeated at least two times. Formation of saliva pellicle on HAP discs was achieved as follows: saliva was collected without conscious stimulation, as described previously (Navazesh, 1993). Saliva was cleared from cellular debris by centrifugation at 10,000 g for 10 minutes. The supernatant (HWS) was collected and used for coating HAP disks with a salivary pellicle. For this purpose, HAP disks were incubated with 4 ml HWS at 37° C. After 3 hrs, disks were rinsed 3 times with distilled water to remove unbound protein. Subsequently, the protective effect of PHS on saliva-coated HAP was tested as described above for bare HAP.

Results

Absorbtion to HAP

We predicted that PHS adsorption onto HAP may give rise to the formation of a protective film that impedes diffusion of polar compounds and modulates microbial adherence. We first verified if PHS indeed binds to HAP. For this, sintered HAP disks, as a model for dental enamel, were treated with PHS at concentrations between 0 and 500 µg/ml. Since PHS is moderately soluble in water, we conducted the binding experiments in Tris-Tween. PHS is completely soluble in Tris-Tween as was verified by determination of the PHS concentration before and after a 10 minutes centrifugation step at 10,000 g. Maximal adsorption occurred at concentrations of 60 µg/ml PHS and higher. Under these conditions approximately 12 µg PHS was adsorbed onto the surface of the disk. After overnight incubation of HAP disks with saliva, followed by incubation with PHS, even higher amounts of PHS adsorbed compared to the control (HAP disks incubated with saliva buffer) (FIG. 14B).

FIG. 12 shows the adsorption over time at a fixed PHS concentration. Within one minute already a substantial amount of PHS was adsorbed. Overall, binding followed a biphasic time course, with an initial fast phase reaching equilibrium within 1 hr, followed by a gradual increase over the next 15 hrs.

Protection Against Demineralization/Erosion

HAP discs, after treatment with a variety of agents (see FIG. 1) were exposed to an erosive challenge of 0.1 M citric acid (pH=3) for 30 minutes. Pretreatment of discs with either bovine serum albumin or with saliva did not result in significant protection. Despite the fact that PHS is poorly soluble in saliva buffer (Veerman et al., 2010) incubation with HAP disks still resulted in substantial protection (70-80% less weight loss compared to the untreated control disks) against a subsequent erosive challenge. Pretreatment with PHS resulted in more than 80% protection against dissolution by citric acid relative to the control disks, which were pretreated with saliva buffer alone, or saliva buffer containing DMSO, which was used for preparing the PHS solution. On the other hand, pre-treatment of HAP disks with 1 mg/ml BSA or whole saliva gave little if any protection against a 30 minute lasting erosive attack. To examine if the protective effects were caused by precipitation of insoluble PHS aggregates onto the HAP disks, we repeated the experiment with PHS dissolved in Tris-Tween. This produced essentially the same protection, corroborating that the observed protection in saliva buffer was not due to precipitation of insoluble PHS aggregates onto the HAP surface. This suggests that PHS formed a protective coating on HAP which protected against acidic attacks by citric acid.

Figure 2:
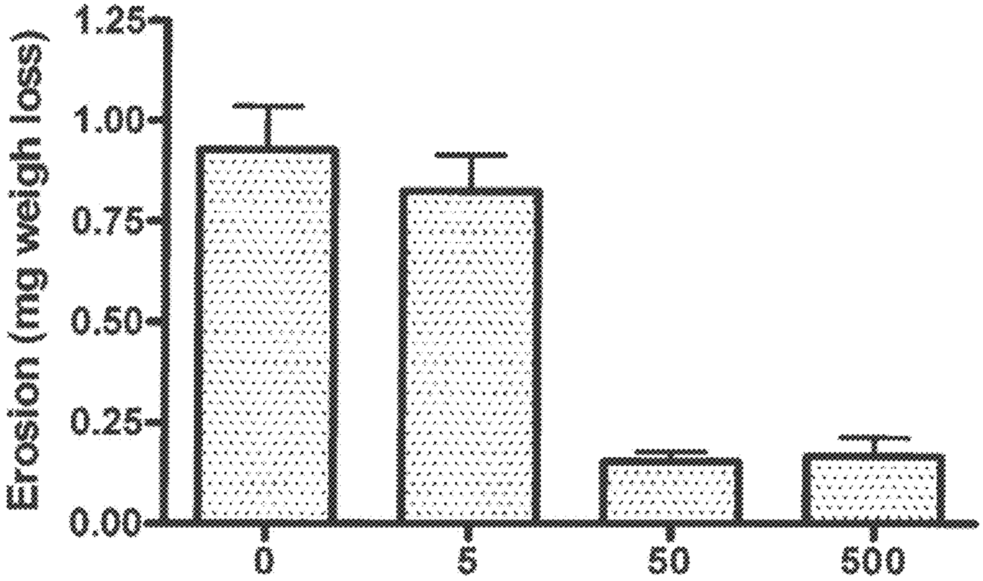
FIG. 2. Anti-erosive effects of PHS at different concentrations.

Next, we tested the minimal concentration at which PHS afforded protection (FIGS. 2 and 13). This revealed comparable protection at 500 and 50 µg/ml. At PHS concentrations >20 µg/ml, virtually maximal protection was achieved. Further lowering the PHS concentration to 5 ug/ml, which is approximately the critical micelle concentration of PHS (Veerman et al, 2007), resulted in a steep decrease in protection. Next we tested the duration of the effect (FIG. 3). This showed that after 1 hour exposure to citric acid, PHS still protected. Pretreatment of discs with the anionic detergent SDS (1%), a compound which is commonly found in toothpastes, did not protect against subsequent exposure to citric acid (not shown), indicating that the protection was caused by the specific molecular properties of PHS.

To examine the effect of the solvent used for preparation of the PHS stock solution, PHS was dissolved in DMSO and ethanol to a concentration of 5 mg/ml. These stock solutions were 10-fold diluted in saliva buffer, with or without sonication. Subsequently HAP disks were incubated for 3 hr with the resultant working solutions, rinsed and exposed to citric acid. No difference between the various conditions used for preparation of the stock solutions were found (FIG. 4). Since dental enamel in situ is covered with a coating of saliva proteins, we tested to which extent this might influence the protection by PHS. We therefore tested the protective effect of PHS on HAP disks that had been preincubated with human saliva, to produce a film of tightly adhering salivary proteins (the salivary pellicle) on the surface of the disks. This revealed that PHS protected saliva-coated HAP to the same extent as it protected uncoated HAP (FIG. 5).

To further explore the structural requirements of the observed effects, protection by two other structurally related sphingosines were tested, sphingosine-phosphate and sphinganine (FIG. 6). Treatment of HAP disks with sphingosine-phosphate (200 μg/ml saliva buffer) did not afford protection against a subsequent erosive attack by citric acid. Treatment of HAP with sphinganine, which compared to phytosphingosine lacks one hydroxyl group at $C_4$ (FIG. 6), protected against citric acid when used in a Tris buffer (FIG. 8), but not when used in a buffer containing phosphate ions. Treatment with sphingosine, sphinganine and phytosphingosine-phosphate at 100 μg/ml in Tris-Tween produced a protection that was comparable to that by PHS. The other lipids tested, including sphingomyelin, phosphatidylcholine and various N-alkyl sphingosines, did not protect HAP.

Effect on Bacterial Adherence

We further tested the effect of PHS on the initial bacterial adherence to HAP disks in vitro with *S. mutans* as a model organism. PHS-coated disks and control disks were submerged in a suspension of *S. mutans* and after 2 hrs the number of adhered bacteria was determined by plating. This revealed a >100-fold decrease in number of adhered bacteria to PHS-coated HAP, compared to base HAP (FIG. 11)).

Protective Effects of Sphingolipids when Present in Citric Acid During the Erosive Attack HA disks were pretreated with buffer or 100 ug/ml PHS for 3 hours (FIG. 15, left two bars) followed with a treatment with 0.1 M citric acid (pH=3.0) for 30 minutes. PHS pre-treatment protects against the erosive effects of citric acid. HA disks were pretreated with either buffer or 100 ug/ml PHS and then exposed to 0.1 M citric acid in the presence of 100 ug/ml PHS for 30 minutes (FIG. 15, right two bars). PHS present in an erosive fluid protects against erosion even with untreated HAP disks. (PHS has no effect on the pH of citric acid.)

Antifouling Properties of Sphingosines

Six different sphingolipids including PHS, PHS phosphate, Sphingosine, Sphinganine, Stearoyl PHS and Sphingomyelin were tested for their antifouling properties against two primary colonizers i.e.—*Streptococcus sanguinis* and *Streptococcus gordonii* and a late colonizer, *Streptococcus mutans.*

HA discs were incubated 0/N with 100 μg/ml lipid at 37° C. Subsequently, the discs were washed to remove unbound lipid. Then the lipid-coated HA discs were incubated for 2 hr with 1.5 ml of ~107 cells/ml. After washing, the adherent bacterial cells were desorbed by sonication and transferred to agar plates. After 48 hr CFUs were counted.

Figure 1:
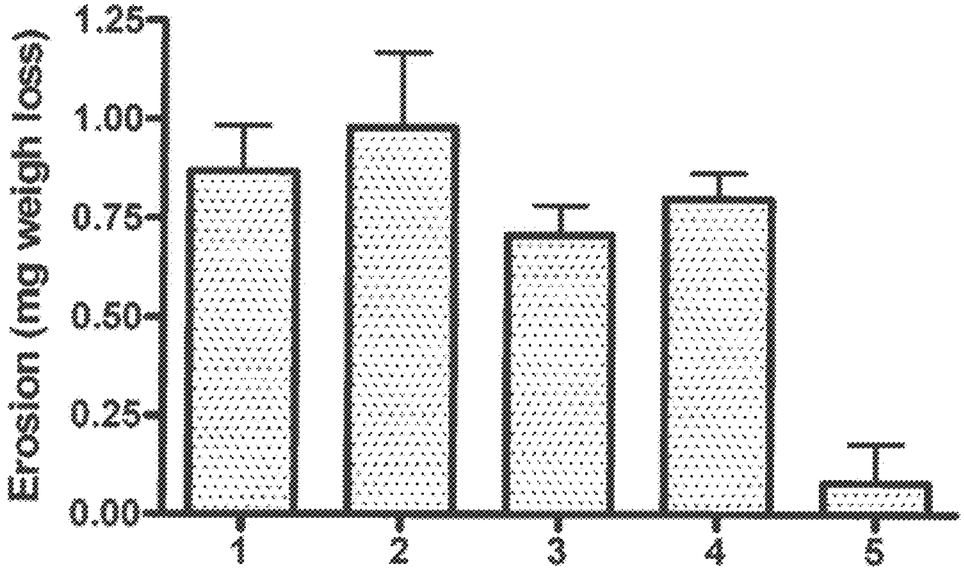
FIG. 1. HAP discs were coated with 1: saliva buffer; 2: saliva buffer supplemented with 1% bovine serum albumin; 3: with human whole saliva; 4: with saliva buffer ((2 mM $K_2HPO_4$, 50 mM KCl, 1 mM $CaCl_2$ & 0.1 mM $MgCl_2$, pH 6.8)) containing 10% DMSO; 5: 500 ug/ml phytosphingosine (PHS) in saliva buffer containing 10% DMSO). After exposure to 0.1 M citric acid (pH 3.0) for 30 minutes, the discs were rinsed, dried and weighed.

For *S. mutans* PHS phosphate and Stearoyl PHS showed clear antifouling activity by almost 2 log CFU/ml. Sphinganine showed a 3 log reduction (FIG. 1).

For *S. sanguinis*, Sphingomyelin showed reduction in bacterial adherence by 1 log value while Sphinganine exhibited reduction by 2 log value (FIG. 2). In case of *S. gordonii*, PHS phosphate and Sphinganine showed reduction by 1.5 log values (FIG. 3).

Materials and Methods

Phytosphingosine (from Doosan Corporation, France) was a kind gift of Dr P. Ekhart (Innopact BV) Sphinganine, 4-hydroxysphinganine-1-phosphate, N-acetoyl 4-hydroxysphinganine, N-octanoyl 4-hydroxysphinganine, N-stearoyl 4-4-hydroxysphinganine (all from *Saccharomyces cerevisiae*), sphingomyelin and sphingosine were obtained from Avanti Polar Lipids (Alabaster, Alabama). Di-myroistyl phosphatidylcholine was obtained from Sigma-Aldrich. Hydroxyapatite disks (diameter 15 mm, height 3 mm), sintered at 1250° C. and with a relative density of 98% were obtained from Swerea, (Stockholm, Sweden). HAP disks manufactured in this way have physical characteristics (e.g. hardness and density) resembling those of enamel (Anderson et al, 2004) and can be used to determine erosive properties of solutions.

Erosion Test

Protection of HAP against erosion was determined essentially as described by Jensdottir et al, (2005), by measuring weight loss from HAP disks before and after immersion in an erosive (acidic) solution using a Sartorius GD503 analytical precision scale. For the erosion experiments, the lateral and bottom surfaces of the disks were covered with nail polish leaving the circular upper surface uncoated. Next, disks were cleaned by sanding with fine sand paper (3M734 P600), rinsed with demineralised water, dried at 37° C. overnight and weighed to determine the initial mass. Stock solutions of lipids were prepared in ethanol to a concentration of 5 mg/ml. These stock solutions were diluted further to the desired concentration in the working buffer. Working solutions of PHS were prepared in saliva buffer (2 mM potassium phosphate, 50 mM KCl, 1 mM $CaCl_2$, 0.1 mM $MgCl_2$, pH 6.8) or in 20 mM Tris (pH 6.8) supplemented with 0.1% Tween 20 (Tris-Tween). HAP disks were placed in the wells of 12 well cell culture plates (Greiner bio-one, Frickenhausen, Germany), to which 1.5 ml of the lipid solutions was added and incubated under gentle shaking for 3 hours at 37° C. After three times rinsing with 4 ml of the incubation buffer to remove unbound lipid, disks were incubated with 4 ml of 0.1 M citric acid (pH=3.0). After 30 minutes incubation at 37° C. under gentle shaking, citric acid was pipetted off and disks were rinsed 3 times with 4 ml demineralized water, dried overnight at 37° C. and weighed. The difference in weight before and after the erosive treatment was taken as a measure for erosion. All incubations were conducted in triplicate and each experiment was repeated at least two times.

Saliva Pellicle

Formation of saliva pellicle on HAP disks was achieved as follows: saliva was collected without conscious stimulation, as described previously (Navazesh et al., 1993). HAP disks were incubated with 4 ml human whole saliva (HWS) at 37° C. After 3 hrs, disks were rinsed 3 times with distilled water to remove unbound protein. Subsequently, the protective effect of lipids on saliva-coated HAP was tested as described above for uncoated HAP disks. The study was approved by the Institutional Ethical Board of the Academic Hospital Vrije Universiteit at Amsterdam and informed consent was obtained from the donor.

PHS Adsorption to HAP

PHS was dissolved in concentrations ranging from 0 to 500 μg/ml in 20 mM Tris buffer supplemented with 0.1% Tween 20 (pH 6.8) (Tris-Tween). Tween 20 was added to keep PHS in solution. Disks were incubated with the PHS solutions for 18 h, and then rinsed with demin water (3 times) to remove unbound PHS. HAP bound PHS was extracted by incubation with 1.5 ml methanol for 90 minutes. Since nail polish dissolved in methanol, in the binding experiments HAP disks were used without nail polish. It was verified that no PHS was adsorbed to the plastic, by conducting control incubations without disks. After evaporation, the residue was dissolved in 250 μl of methanol. To 100 of this solution 25 μl ortho-phtaldialdehyde reagent (OPA, Sigma-Aldrich) to enable fluorimetric quantification of bound PHS. Fluorescence was measured on a Fluostar microplate reader at excitation/emission wavelengths of 380 nm/450 nm. Absolute quantities were determined by reference to a standard curve of PHS. All incubations were conducted in triplicate and the experiment was repeated two times.

Bacterial Adhesion

Adhesion of bacteria to HAP discs was investigated using the active attachment model, essentially as described previously (Exterkate et al., 2010). This model consists of a custom made stainless steel lid with 24 clamps that contained the PHS- and buffer-treated HAP discs as substratum for adhesion of *S. mutans*. HAP discs (diameter: 9.7 mm diameter; thickness: 1.7 mm Himed, NY, USA) were incubated overnight at 30° C. in 20 mM Tris, 0.1% Tween 20, pH 6.8, with or without 100 μg/ml PHS. Subsequently the HAP discs were washed three times by transferring the lid to a 24 well plate containing 1.6 ml of buffer and moved 10 times up and down to remove excess PHS. *S mutans* was cultured overnight in BHI medium and diluted 1:10 in half-strength BHI (18.5 g BHI/l, 50 Mm/l PIPES, pH 7.0) to a final density of approximately $10^8$ cells/ml. The lid with the HAP disks was placed on top of the 24 well plate containing 1.5 ml of diluted bacterial suspension and incubated anaerobically for 2 hr at 37° C. The HAP discs were washed twice by transferring the lid to plate containing 1.6 ml cysteine peptone water (CPW), to remove the non-adherent bacteria. Subsequently the discs were removed from the lid and transferred to 2 ml CPW and the attached layer of bacteria was dispersed by sonification for 2 min with 1 s pulses. The resulting suspension was plated in different dilutions on BHI plates and incubated anaerobically for 48 hr at 37° C. before CFU were counted.

The invention claimed is:

1. A method for reducing dental hypersensitivity or treating dental erosion in a human subject in need thereof, the method comprising: a step of coating a tooth of the human subject with a composition comprising at least one active ingredient capable of forming a barrier on the tooth, the at least one active ingredient being selected from phytosphingosine or a conjugate of phytosphingosine;

wherein the at least one active ingredient is present in the composition in an amount from 20 pg/ml to 500 pg/ml; and wherein the step of coating the tooth results in the formation of a barrier on the tooth and the reduction of dental hypersensitivity or the treatment of dental erosion.

2. The method of claim 1, wherein the at least one active ingredient is phytosphingosine.

3. The method of claim 1, wherein the composition further comprises hydroxyapatite nanoparticles.

4. The method of claim 1, wherein the composition is selected from toothpaste, chewing gum, or mouthwash.

* * * * *